US008532938B2

(12) United States Patent
Jung et al.

(10) Patent No.: US 8,532,938 B2
(45) Date of Patent: Sep. 10, 2013

(54) TESTING-DEPENDENT ADMINISTRATION OF A NUTRACEUTICAL

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1192 days.

(21) Appl. No.: 11/291,532

(22) Filed: Nov. 30, 2005

(65) Prior Publication Data
US 2007/0150306 A1 Jun. 28, 2007

Related U.S. Application Data

(63) Continuation-in-part of application No. 11/283,548, filed on Nov. 17, 2005, and a continuation-in-part of application No. 11/291,482, filed on Nov. 30, 2005.

(51) Int. Cl.
*G06Q 10/00* (2012.01)
*A61B 5/00* (2006.01)

(52) U.S. Cl.
USPC .............................. 702/22; 702/19

(58) Field of Classification Search
USPC ....... 702/19, 22, 188–189; 703/11; 436/501; 435/7.1
See application file for complete search history.

(56) References Cited

U.S. PATENT DOCUMENTS

| | | | |
|---|---|---|---|
| 4,567,185 A | 1/1986 | Sackner | |
| 4,838,275 A | 6/1989 | Lee | |
| 4,847,764 A | 7/1989 | Halvorson | |
| 4,857,716 A | 8/1989 | Gombrich et al. | |
| 5,054,493 A | 10/1991 | Cohn et al. | |
| 5,279,294 A | 1/1994 | Anderson et al. | |
| 5,300,302 A | 4/1994 | Tachon et al. | |
| 5,307,263 A | 4/1994 | Brown | |
| 5,495,961 A | 3/1996 | Maestre | |
| 5,537,313 A * | 7/1996 | Pirelli | 705/28 |
| 5,672,154 A | 9/1997 | Sillén et al. | |
| 5,692,502 A | 12/1997 | Alpert | |
| 5,700,998 A | 12/1997 | Palti | |
| 5,710,578 A | 1/1998 | Beauregard et al. | |
| 5,737,539 A | 4/1998 | Edelson et al. | |
| 5,770,226 A | 6/1998 | Hughes, Jr. et al. | |

(Continued)

FOREIGN PATENT DOCUMENTS

| | | |
|---|---|---|
| WO | WO 97/14393 | 4/1997 |
| WO | WO 99/45354 | 9/1999 |

(Continued)

OTHER PUBLICATIONS

U.S. Appl. No. 11/355,517, Jung et al.

(Continued)

*Primary Examiner* — Manuel L Barbee

(57) ABSTRACT

A method, system, and computer program product are described for receiving a test result of a state of a subject and indicating an amount of a nutraceutical partly based on the test result and partly based on a regimen.

30 Claims, 14 Drawing Sheets

(56) References Cited

U.S. PATENT DOCUMENTS

| | | | |
|---|---|---|---|
| 5,807,579 A | 9/1998 | Vilkov et al. |
| 5,873,369 A | 2/1999 | Laniado et al. |
| 5,882,931 A | 3/1999 | Petersen |
| 5,907,291 A | 5/1999 | Chen et al. |
| 5,940,801 A | 8/1999 | Brown |
| 5,954,640 A | 9/1999 | Szabo |
| 5,955,269 A | 9/1999 | Ghai et al. |
| 5,995,938 A | 11/1999 | Whaley |
| 6,021,202 A | 2/2000 | Anderson et al. |
| 6,024,699 A | 2/2000 | Surwit et al. |
| 6,035,230 A | 3/2000 | Kang et al. |
| 6,117,073 A | 9/2000 | Jones et al. |
| 6,128,534 A | 10/2000 | Park et al. |
| 6,139,494 A | 10/2000 | Cairnes |
| 6,161,095 A | 12/2000 | Brown |
| 6,188,988 B1 | 2/2001 | Barry et al. |
| 6,227,371 B1 | 5/2001 | Song |
| 6,287,595 B1 | 9/2001 | Loewy et al. |
| 6,383,136 B1 | 5/2002 | Jordan |
| 6,397,190 B1 | 5/2002 | Goetz |
| 6,421,650 B1 | 7/2002 | Goetz et al. |
| 6,450,956 B1 | 9/2002 | Rappaport et al. |
| 6,468,805 B1 | 10/2002 | Smith |
| 6,510,430 B1 | 1/2003 | Oberwager et al. |
| 6,529,446 B1 | 3/2003 | de la Huerga |
| 6,541,478 B1 | 4/2003 | O'Malley et al. |
| 6,589,169 B1 | 7/2003 | Surwit et al. |
| 6,616,606 B1 | 9/2003 | Petersen et al. |
| 6,656,122 B2 * | 12/2003 | Davidson et al. ............ 600/454 |
| 6,671,818 B1 | 12/2003 | Mikurak |
| 6,699,193 B2 | 3/2004 | Crutchfield et al. |
| 6,764,831 B2 | 7/2004 | Cameron, Sr. et al. |
| 6,770,029 B2 * | 8/2004 | Iliff .............................. 600/300 |
| 6,790,198 B1 | 9/2004 | White et al. |
| 6,951,545 B2 | 10/2005 | Smith et al. |
| 6,955,873 B1 | 10/2005 | Blum |
| 7,005,447 B2 | 2/2006 | Ahotupa et al. |
| 7,016,752 B1 | 3/2006 | Ruben et al. |
| 7,029,441 B2 | 4/2006 | Dodds |
| 7,135,616 B2 | 11/2006 | Heard et al. |
| 7,136,820 B1 | 11/2006 | Petrus |
| 7,169,432 B2 | 1/2007 | Tanaka et al. |
| 7,172,897 B2 | 2/2007 | Blackburn et al. |
| 7,193,128 B2 | 3/2007 | Copenhaver et al. |
| 7,197,492 B2 | 3/2007 | Sullivan |
| 7,216,343 B2 | 5/2007 | Das et al. |
| 7,280,975 B1 | 10/2007 | Donner |
| 7,351,739 B2 | 4/2008 | Ho et al. |
| 7,376,585 B2 | 5/2008 | Haller |
| 7,379,167 B2 | 5/2008 | Mawhirt et al. |
| 7,418,399 B2 | 8/2008 | Schaeffer et al. |
| 7,483,839 B2 | 1/2009 | Mayaud |
| 7,490,085 B2 | 2/2009 | Walker et al. |
| 7,502,666 B2 | 3/2009 | Siegel et al. |
| 7,635,594 B2 | 12/2009 | Holmes et al. |
| 2001/0003177 A1 | 6/2001 | Schena et al. |
| 2001/0037220 A1 | 11/2001 | Merry et al. |
| 2002/0004749 A1 | 1/2002 | Froseth et al. |
| 2002/0016719 A1 | 2/2002 | Nemeth et al. |
| 2002/0019784 A1 | 2/2002 | Ritz |
| 2002/0027164 A1 | 3/2002 | Mault et al. |
| 2002/0032580 A1 | 3/2002 | Hopkins |
| 2002/0032582 A1 | 3/2002 | Feeney, Jr. et al. |
| 2002/0032583 A1 | 3/2002 | Joao |
| 2002/0032620 A1 | 3/2002 | Benz et al. |
| 2002/0055856 A1 | 5/2002 | Adams |
| 2002/0059030 A1 | 5/2002 | Otworth et al. |
| 2002/0065682 A1 | 5/2002 | Goldenberg |
| 2002/0070226 A1 | 6/2002 | Liff et al. |
| 2002/0077850 A1 | 6/2002 | McMenimen et al. |
| 2002/0091546 A1 | 7/2002 | Christakis et al. |
| 2002/0091991 A1 | 7/2002 | Castro |
| 2002/0095238 A1 | 7/2002 | Ahlin et al. |
| 2002/0100762 A1 | 8/2002 | Liff et al. |
| 2002/0106429 A1 | 8/2002 | Mudar et al. |
| 2002/0128259 A1 | 9/2002 | Ghazzi et al. |
| 2002/0143434 A1 | 10/2002 | Greeven et al. |
| 2002/0147317 A1 | 10/2002 | Bentsen et al. |
| 2002/0156651 A1 | 10/2002 | Florio et al. |
| 2002/0156683 A1 | 10/2002 | Stoutenburg et al. |
| 2002/0173875 A1 | 11/2002 | Wallace et al. |
| 2002/0192310 A1 | 12/2002 | Bland et al. |
| 2002/0194226 A1 | 12/2002 | Sheth et al. |
| 2002/0194502 A1 | 12/2002 | Sheth et al. |
| 2003/0004403 A1 * | 1/2003 | Drinan et al. ............... 600/301 |
| 2003/0005445 A1 | 1/2003 | Schein et al. |
| 2003/0019165 A1 | 1/2003 | Gallant et al. |
| 2003/0028399 A1 | 2/2003 | Davis et al. |
| 2003/0032868 A1 | 2/2003 | Graskov et al. |
| 2003/0036683 A1 | 2/2003 | Kehr et al. |
| 2003/0055531 A1 | 3/2003 | Liff et al. |
| 2003/0061123 A1 | 3/2003 | McMenimen et al. |
| 2003/0069757 A1 | 4/2003 | Greenberg |
| 2003/0073931 A1 | 4/2003 | Boecker et al. |
| 2003/0074218 A1 | 4/2003 | Liff et al. |
| 2003/0082544 A1 | 5/2003 | Fors et al. |
| 2003/0086338 A1 | 5/2003 | Sastry et al. |
| 2003/0088333 A1 | 5/2003 | Liff et al. |
| 2003/0105552 A1 | 6/2003 | Lunak et al. |
| 2003/0114475 A1 | 6/2003 | Fox et al. |
| 2003/0121929 A1 | 7/2003 | Liff et al. |
| 2003/0125837 A1 | 7/2003 | Walace et al. |
| 2003/0135388 A1 | 7/2003 | Martucci et al. |
| 2003/0137067 A1 | 7/2003 | Cooper et al. |
| 2003/0139655 A1 | 7/2003 | Dodds |
| 2003/0158756 A1 | 8/2003 | Abramson |
| 2003/0163353 A1 | 8/2003 | Luce et al. |
| 2003/0171950 A1 | 9/2003 | Kilgannon et al. |
| 2003/0189058 A1 | 10/2003 | Liff et al. |
| 2003/0191670 A1 | 10/2003 | Hatcher et al. |
| 2003/0204412 A1 | 10/2003 | Brier |
| 2003/0207270 A1 | 11/2003 | Kung et al. |
| 2003/0216831 A1 | 11/2003 | Hart et al. |
| 2003/0219812 A1 | 11/2003 | Quay et al. |
| 2003/0220848 A1 | 11/2003 | Behrendt |
| 2003/0229455 A1 | 12/2003 | Bevilacqua et al. |
| 2003/0233250 A1 | 12/2003 | Joffe et al. |
| 2004/0032330 A1 | 2/2004 | Hoffman |
| 2004/0064342 A1 | 4/2004 | Browne et al. |
| 2004/0075272 A1 | 4/2004 | Kaufman |
| 2004/0078220 A1 | 4/2004 | Jackson |
| 2004/0078236 A1 | 4/2004 | Stoodley et al. |
| 2004/0088187 A1 | 5/2004 | Chudy et al. |
| 2004/0107022 A1 | 6/2004 | Gomez |
| 2004/0111298 A1 | 6/2004 | Schoenberg |
| 2004/0121767 A1 | 6/2004 | Simpson et al. |
| 2004/0122707 A1 | 6/2004 | Sabol et al. |
| 2004/0122790 A1 | 6/2004 | Walker et al. |
| 2004/0133705 A1 | 7/2004 | Broussard et al. |
| 2004/0138921 A1 | 7/2004 | Broussard et al. |
| 2004/0138926 A1 | 7/2004 | Ishikawa et al. |
| 2004/0143403 A1 | 7/2004 | Brandon et al. |
| 2004/0154688 A1 | 8/2004 | Geltser et al. |
| 2004/0158507 A1 | 8/2004 | Meek, Jr. et al. |
| 2004/0176984 A1 | 9/2004 | White et al. |
| 2004/0188523 A1 | 9/2004 | Lunak et al. |
| 2004/0188524 A1 | 9/2004 | Lunak et al. |
| 2004/0193316 A1 | 9/2004 | Lunak et al. |
| 2004/0210341 A1 | 10/2004 | Wallace et al. |
| 2004/0215486 A1 | 10/2004 | Braverman |
| 2004/0220498 A1 | 11/2004 | Li et al. |
| 2004/0225203 A1 | 11/2004 | Jemison et al. |
| 2004/0243437 A1 | 12/2004 | Grace et al. |
| 2004/0243441 A1 | 12/2004 | Bocionek et al. |
| 2004/0254868 A1 | 12/2004 | Kirkland et al. |
| 2005/0010416 A1 | 1/2005 | Anderson et al. |
| 2005/0021413 A1 | 1/2005 | Berry et al. |
| 2005/0027570 A1 | 2/2005 | Maier et al. |
| 2005/0033121 A1 | 2/2005 | Modrovich |
| 2005/0038558 A1 | 2/2005 | Keene |
| 2005/0062238 A1 | 3/2005 | Broadfield et al. |
| 2005/0065645 A1 | 3/2005 | Liff et al. |
| 2005/0090718 A1 * | 4/2005 | Dodds ........................... 600/300 |
| 2005/0101841 A9 | 5/2005 | Kaylor et al. |

| | | | |
|---|---|---|---|
| 2005/0102159 A1 | 5/2005 | Mondshine | |
| 2005/0118202 A1 | 6/2005 | Yamashita et al. | |
| 2005/0147667 A1 | 7/2005 | Rines | |
| 2005/0158401 A1 | 7/2005 | Morris | |
| 2005/0192487 A1 | 9/2005 | Cosentino et al. | |
| 2005/0216313 A1 | 9/2005 | Claud et al. | |
| 2005/0216390 A1 | 9/2005 | Snider et al. | |
| 2005/0240305 A1 | 10/2005 | Bogash et al. | |
| 2005/0256745 A1 | 11/2005 | Dalton | |
| 2005/0260610 A1 | 11/2005 | Kurtz et al. | |
| 2005/0260679 A1 | 11/2005 | Kellerman et al. | |
| 2005/0261255 A1 | 11/2005 | Serhan et al. | |
| 2005/0267356 A1 | 12/2005 | Ramasubramanian et al. | |
| 2005/0271596 A1 | 12/2005 | Friedman et al. | |
| 2006/0047538 A1 | 3/2006 | Condurso et al. | |
| 2006/0064250 A1* | 3/2006 | Goldstein | 702/19 |
| 2006/0090765 A1 | 5/2006 | Surina | |
| 2006/0111944 A1 | 5/2006 | Sirmans, Jr. et al. | |
| 2006/0129324 A1 | 6/2006 | Rabinoff et al. | |
| 2006/0161443 A1 | 7/2006 | Rollins | |
| 2006/0177637 A1 | 8/2006 | Kimura | |
| 2006/0240150 A1 | 10/2006 | Delaney et al. | |
| 2006/0248468 A1 | 11/2006 | Constantine et al. | |
| 2006/0254580 A1 | 11/2006 | Chalmers et al. | |
| 2006/0260679 A1 | 11/2006 | Aratani et al. | |
| 2006/0264780 A1 | 11/2006 | Holmes et al. | |
| 2006/0287891 A1 | 12/2006 | Grasso et al. | |
| 2007/0035403 A1 | 2/2007 | Krishna et al. | |
| 2007/0068959 A1* | 3/2007 | D'Silva | 221/7 |
| 2007/0087048 A1 | 4/2007 | Abrams et al. | |
| 2007/0136092 A1 | 6/2007 | Jung et al. | |
| 2007/0161076 A1 | 7/2007 | Halden | |
| 2008/0097784 A1 | 4/2008 | Miller et al. | |
| 2008/0139907 A1* | 6/2008 | Rao et al. | 600/323 |
| 2008/0299013 A1 | 12/2008 | Trieu et al. | |
| 2010/0081144 A1 | 4/2010 | Holmes et al. | |

FOREIGN PATENT DOCUMENTS

| | | |
|---|---|---|
| WO | WO 00/60362 | 10/2000 |
| WO | WO 01/79529 A1 | 10/2001 |
| WO | WO 2005/062849 A2 | 7/2005 |
| WO | WO 2007/061838 A2 | 5/2007 |

OTHER PUBLICATIONS

U.S. Appl. No. 11/339,316, Jung et al.
U.S. Appl. No. 11/314,949, Jung et al.
U.S. Appl. No. 11/314,764, Jung et al.
U.S. Appl. No. 11/291,482, Jung et al.
U.S. Appl. No. 11/285,753, Jung et al.
U.S. Appl. No. 11/285,500, Jung et al.
PCT International Search Report; International App. No. PCT/US 06/44664; Apr. 14, 2008; pp. 1-3.
PCT International Search Report; International App. No. PCT/US07/25379; pp. 1-2; dated May 13, 2008.
PCT International Search Report; International App. No. PCT/US07/25417; pp. 1-3; dated May 14, 2008.
PCT International Search Report; International App. No. PCT/US07/25417; pp. 1-2; dated May 19, 2008.
PCT International Search Report; International App. No. PCT/US2007/025450; pp. 1-2; dated May 23, 2008.
PCT International Search Report; International App. No. PCT/US06/47835; pp. 1-2; dated Jul. 14, 2008.
PCT International Search Report; International App. No. PCT/ US 06/44269; 2 pages; Sep. 18, 2007.
Felkey, Bill G.; Berger, Bruce A.; Krueger, Kem P.; "The Pharmacists's Role in Treatment Adherence—Part 5: The Impact of Pharmacy-Specific Technology"; U.S. Pharmacist; bearing a date of 2005, 2000-2005; and a posted date of Aug. 18, 2005; pp. 36-39 (pp. 1-6); vol. 30:08; Jobson Publishing, L.L.C.; located at: http://www.uspharmacist.com/index.asp?show=article&page=8_1547.htm; printed on Nov. 13, 2005.
"Heart-Help's Handbook . . . Living with CM & CHF (Cardiomyopathy & Congestive Heart Failure)"; bearing a date of Sep. 23, 2001; pp. 1-5; located at: http://www.heart-help.net/handbook.html; printed on Nov. 13, 2005.

"On Time-RX Medication Reminders"; bearing a date of 2000-2004; pp. 1-4; AmeliaPlex, Inc., Orlando, FL; located at: http://www.ontimerx.com/PDA/index.asp; printed on Nov. 13, 2005.
Evans, R. Scott, Ph.D. et al., "A Computer-Assisted Management Program for Antibiotics and Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C.C., J.F.L., J.P.B.). Critical Care (T.P.C., L.K.W., J.F.O.,), and Medical Informatics (R.S.E.), LDS Hospital, Salt Lake City, UT.
Lagally, E.T. et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.
Leibovici, Leonard et al.; "A Causal Probabilistic Network for Optimal Treatment of Bacterial Infections"; IEEE Transactions on Knowledge and Data Engineering; bearing a date of Jul./Aug. 2000; pp. 517-528; vol. 12, No. 4; © 2000 IEEE.
Edible Science; bearing dates of 2005-2010; pp. 1-2; located at: http://www.ediblesciencecom; printed on May 13, 2010.
Fightermins; bearing a date of 2010; 1 page; located at: http://www.fightermins.com/index.jsp; printed on May 13, 2010.
Ideal Health; "Custom Essentials"; "The Priva Test"; bearing a date of 2010; total of 5 pages; located at: http://www.idealhealth.com; printed on May 13, 2010; The Trump Network.
I-Vita; bearing a date of 2009; 1 page; located at: http://www.mynutrapack.com/index.html; printed on May 13, 2010.
LifeScript; bearing dates of 1998-2010; 1 page; located at:http://vitamins.lifescript.com/Begin.asp?BID=14971&PROMO=zluswiec; printed on May 13, 2010.
Mindell, Earl, Dr.; Vitaganic "Custom-Made Multivitamins"; bearing dates of 2005-2010; 1 page; located at: http://drmindell.vitaganic.com/; printed on May 13, 2010.
My Vitamin Clinic; bearing a date of 2010; 1 page; located at: http://www.myvitaminclinic.com/index.jsp; printed on May 13, 2010.
MyNutraPack; 1 page; located at: http://www.mynutrapack.com/index.html; printed on May 25, 2010.
MyVitaminRx; bearing a date of 2007; 1 page; located at: http://www.myvitaminsrx.com/CustomNutrition.aspx?ID=MoonlightSpa; printed on May 13, 2010.
Nature Made; pp. 1-2; located at: http://www.naturemade.com/; printed on May 13, 2010.
NutriHerb; bearing dates of 2001-2009; pp. 1-2; Nutri Herb, Inc.; located at:http://www.nutriherb.net/custom_made_to_order_herbal_vitamins_supplements.html; printed on May 13, 2010.
Pharmative LLC; 1 page; located at: http://www.pharmavite.com/index.asp; printed on May 13, 2010.
"Pharmavite LLC Launches New Direct-To-Consumer Company" Press Release; Pharmavite LLC; bearing a date of Sep. 4, 2009; 1 page; located at: http://www.pharmavite.com/MediaCenter/MC_PR.asp?ID=164; printed on May 13, 2010.
Signature Supplements; bearing a date of 2009; pp. 1-2; located at: http://www.signaturesupplements.com/jsp/main/index.jsp; printed on May 13, 2010; Signature Supplements.
Soyjoy®; bearing a date of 2010; 1 page; located at: http://www.soyjoy.com/index.aspx; printed on May 13, 2010; Pharmavite LLC.
Total Health Nutrients; pp. 1-2; located at: http://www.totathealthnutrients.com/ph/index.html; printed on May 13, 2010.
VitaminID.com; bearing a date of 2010; 1 page; located at: http://www.vitaminid.com/webapp/wcs/stores/servlet/StoreView?storeId=201&langId=-1; printed on May 25, 2010; Pharmavite Direct LLC.
Vitamins On Demand; bearing a date of 2010; 1 page; located at: http://www.vitaminsondemand.com/?gclid=CNbygPut9aACFRYhDQodyGkivw; printed on May 13, 2010.
VitaXact; bearing a date of 2009; 1 page; located at: http://www.vitaxact.com; printed on May 13, 2010.
Weil, Andrew, M.D.; "Dr. Weil's Vitamin Advisor & Complete Program Supplements"; bearing a date of 2010; 1 page; located at: https://www.drweilvitaminadvisor.com/drw/ecs/Va2/land_goog_08girl.html?aid=999910&aparam=TSAsGoogleApr10VA_vitamins&refcd=GO000000101882154s_vitamins&tsacr=GO3784957603&gclid=CM3NpLzm9aACFRYhDQodyGkivw; printed on May 13, 2010; Weil Lifestyle Custom Pak.

UK Intellectual Property Office Examination Report Under Section 18(3); Appl. No. GB1000316.8; Jul. 26, 2011; pp. 1-3.

Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.

Sriskanthan, N. and Subramanian, K. R.; "Braille Display Terminal for Personal Computers"; IEEE Transactions on Consumer Electronics; May 1990; pp. 121-128; vol. 36, No. 2; IEEE.

Walt et al.; "Biological Warfare, A Host of Detection Strategies Have Been Developed, But Each Has Significant Limitations"; Analytical Chemistry; bearing a date of Dec. 1, 2000; pp. 738A-747A.

U.S. Appl. No. 13/374,765, Jung et al.

U.S. Appl. No. 11/314,945, Jung et al.

Smith, Stevie; "New Chip Identifies Bird Flu in Humans"; The Tech Herald.com, WOTR Limited; 2008; located at: www.thetechherald.com/article/php200813/520/new-chip-identifies-bird-flu-in-humans; Bearing a date of Mar. 25, 2008; printed on Sep. 8, 2008; pp. 1-6.

"Microsoft Press Computer Dictionary: The Comprehensive Standard for Business, School, Library, and Home"; bearing a date of Nov. 1, 1993; 1 page; Edition 2; Microsoft Press; IBSN: 9781556155970 (whole book not provided).

Roberts et al.; "Nutraceuticals: The Complete Encyclopedia of Supplements, Herbs, Vitamins and Healing Foods"; American Nutraceutical Association; bearing a date of Jan. 1, 2001; pp. 1-3 (669 pages, not provided); Perigee Trade; IBSN: 0399526323 (whole book not provided).

* cited by examiner

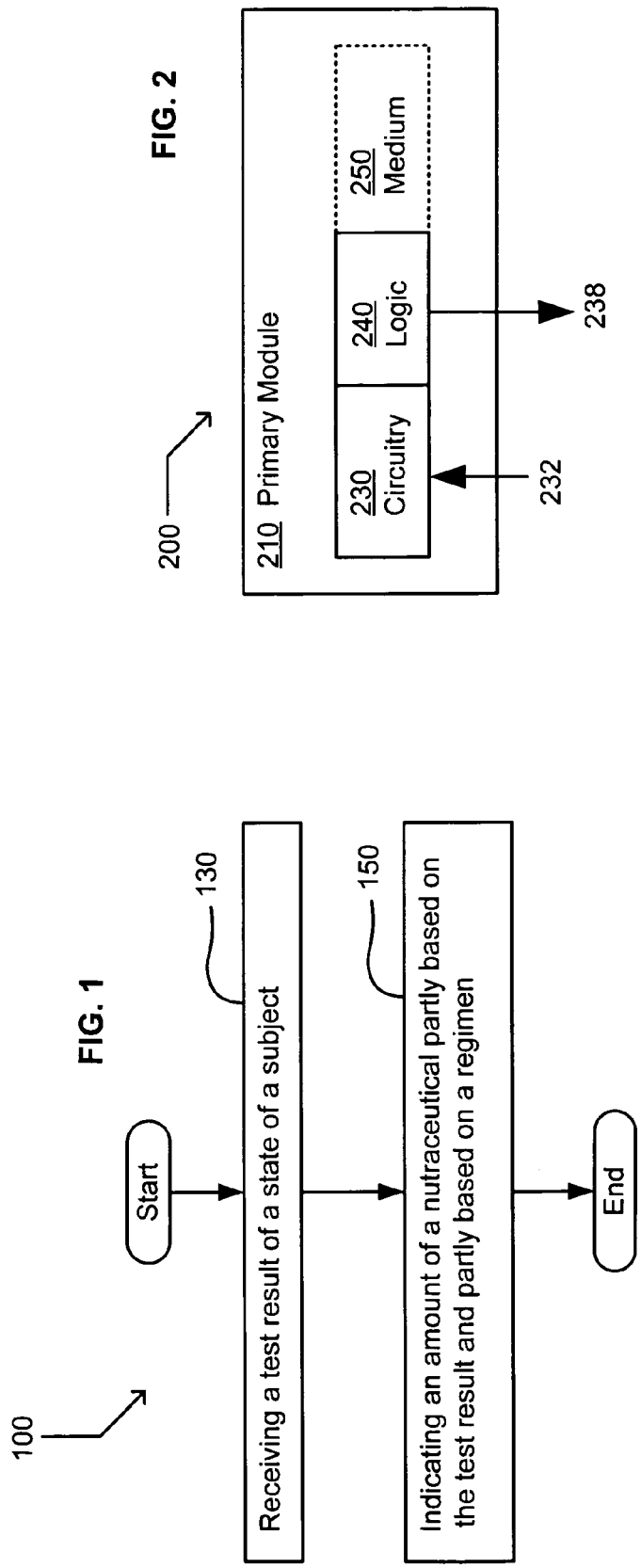

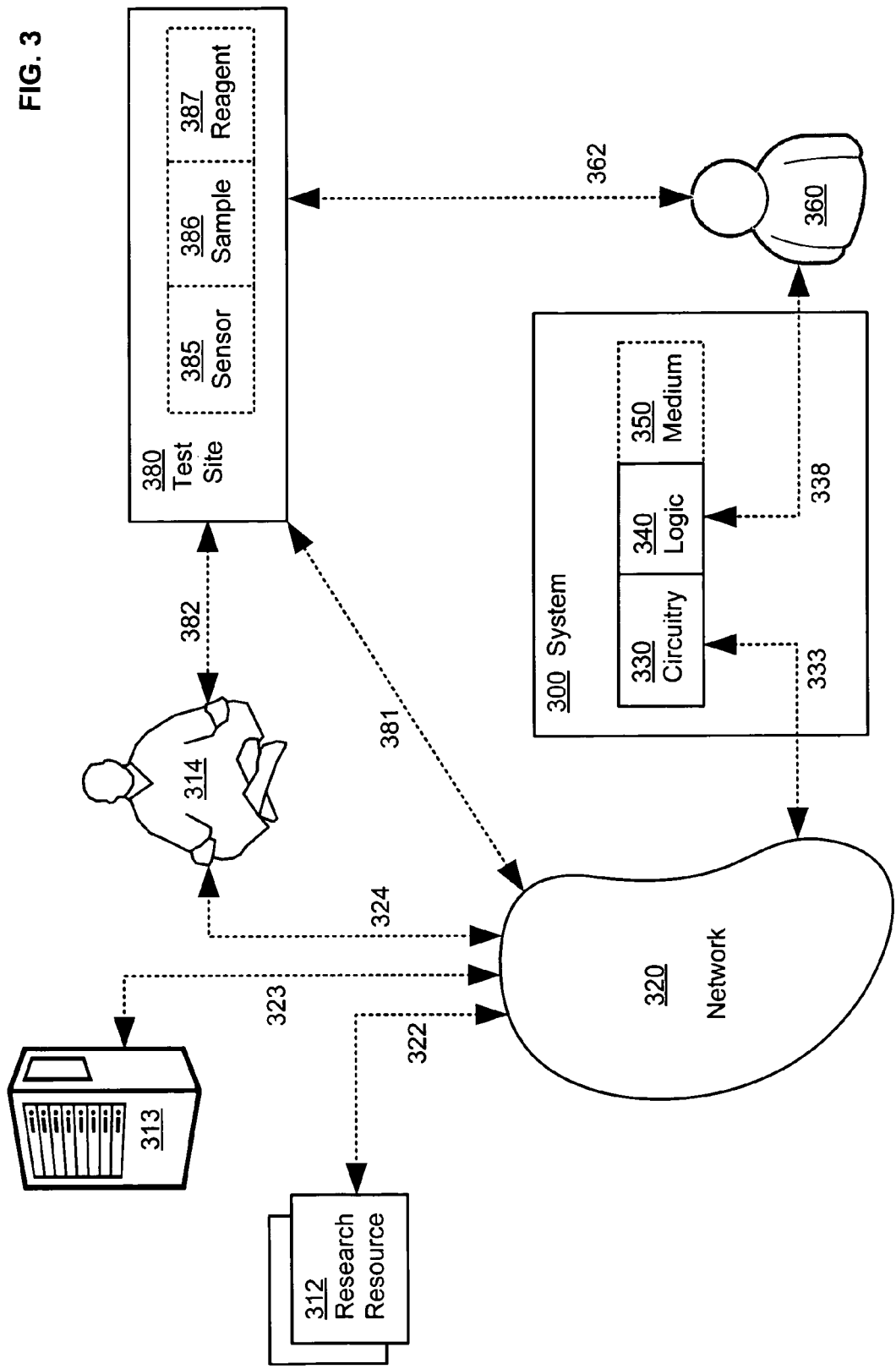

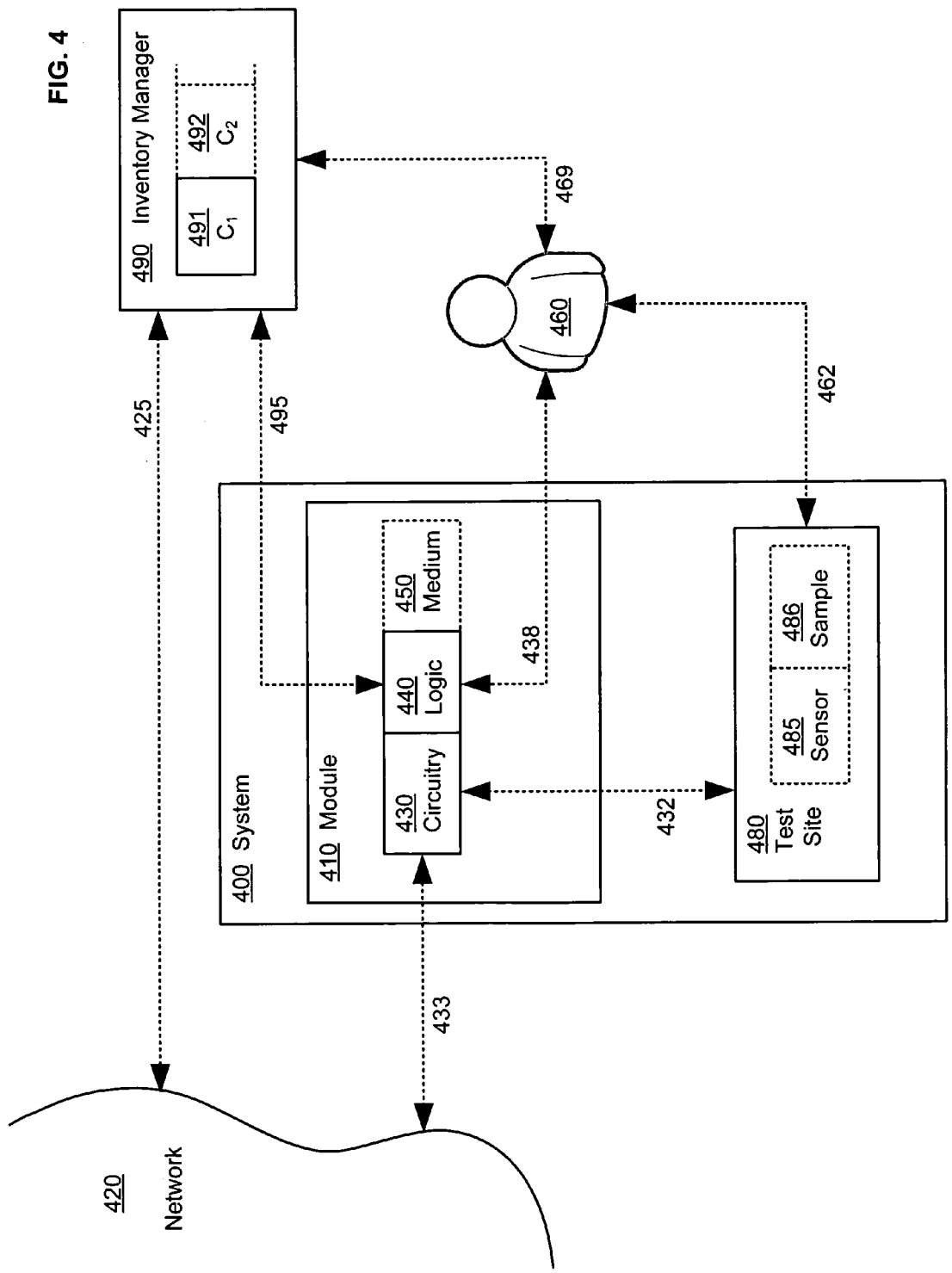

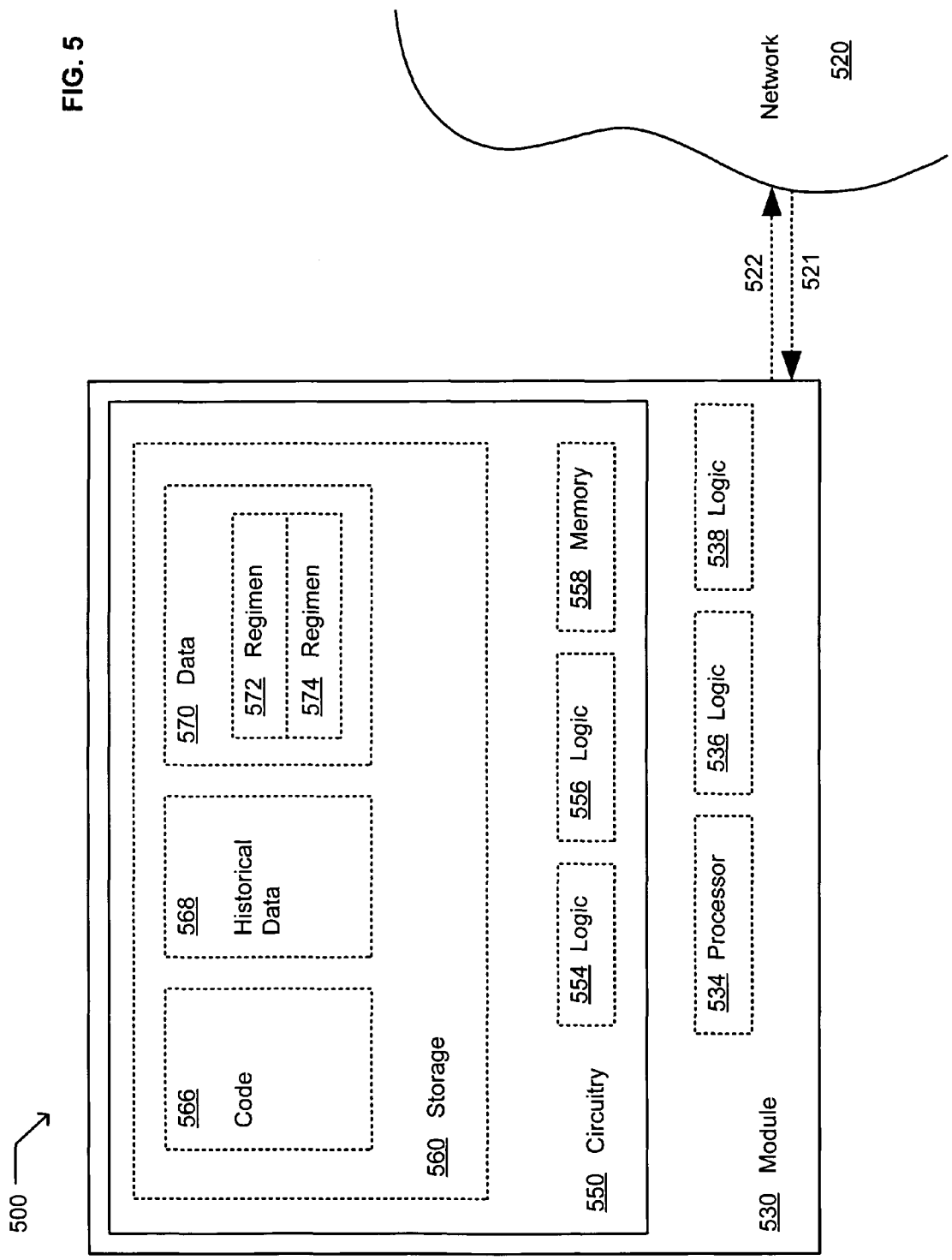

TESTING-DEPENDENT ADMINISTRATION OF A NUTRACEUTICAL

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

Related Applications:

1. For purposes of the USPTO extra-statutory requirements, the present application constitutes a continuation-in-part of U.S. patent application Ser. No. 11/283,548, entitled PROVIDING ASSISTANCE RELATED TO HEALTH, naming Edward K. Y. Jung, Joyce A. Levien, Robert W. Lord, Mark A. Malamud, John D. Rinaldo, Jr., Clarence T. Tegreene and Lowell L. Wood, Jr. as inventors, filed Nov. 17, 2005, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 11/291,482 entitled GENERATING A NUTRACEUTICAL REQUEST FROM AN INVENTORY, naming Edward K. Y. Jung, Joyce A. Levien, Robert W. Lord, Mark A. Malamud, John D. Rinaldo, Jr., Clarence T. Tegreene and Lowell L. Wood, Jr. as inventors, filed Nov. 30, 2005, which is currently co-pending, or is an application of which a currently co-pending application is entitled to the benefit of the filing date.

SUMMARY

An embodiment provides a method. In one implementation, the method includes but is not limited to receiving a test result of a state of a subject and indicating an amount of a nutraceutical partly based on the test result and partly based on a regimen. In addition to the foregoing, other communication method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for receiving a test result of a state of a subject and a module for indicating an amount of a nutraceutical partly based on the test result and partly based on a regimen. In addition to the foregoing, other system aspects are described in the claims, drawings, and text forming a part of the present disclosure.

An embodiment provides another system. In one implementation, the other system includes but is not limited to a computing device and one or more instructions that when executed on the computing device cause the computing device to perform at least one of receiving a test result of a state of a subject and indicating an amount of a nutraceutical partly based on the test result and partly based on a regimen. In addition to the foregoing, other system aspects are described in the claims, drawings, and text forming a part of the present disclosure.

An embodiment provides a computer program product. In one implementation, the computer program product includes but is not limited to a signal-bearing medium bearing at least one of one or more instructions for receiving a test result of a state of a subject and one or more instructions for indicating an amount of a nutraceutical partly based on the test result and partly based on a regimen. In addition to the foregoing, other computer program product aspects are described in the claims, drawings, and text forming a part of the present disclosure.

In addition to the foregoing, various other embodiments are set forth and described in the text (e.g., claims and/or detailed description) and/or drawings of the present description.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BRIEF DESCRIPTION OF THE FIGURES

FIG. 1 illustrates an operational flow representing operations that produce (at least) an indication of an amount of a nutraceutical.

FIG. 2 shows an example system in schematic form, a hardware implementation able to perform variants of the flow of FIG. 1.

FIG. 3 shows another example system able to perform the flow of FIG. 1.

FIG. 4 shows another example system able to perform the flow of FIG. 1, optionally used in combination with the system of FIG. 2 or FIG. 3.

FIG. 5 shows another example system able to perform the flow of FIG. 1, optionally used in combination with the system of FIG. 2, 3, or 4.

DESCRIPTION

Figure 6:
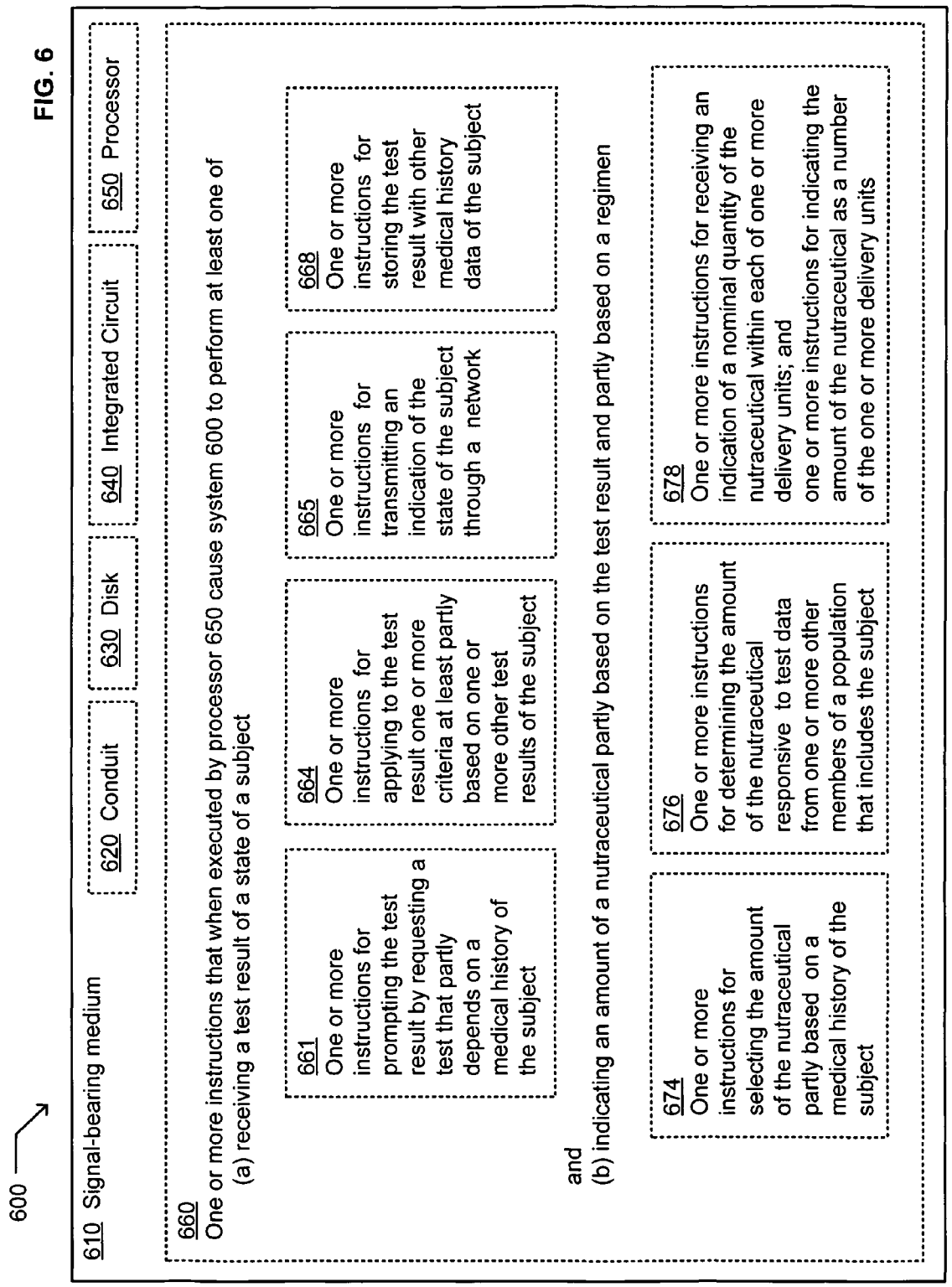
FIG. 6 shows a system including a signal bearing medium that can optionally comprise a conduit, a disk, or an integrated circuit.

FIG. 1 shows an operational flow 100 representing example operations that produce an indication of an amount of a nutraceutical, such as by indicating a rate or otherwise expressing a quantity of a dispensation that includes the nutraceutical. Flow 100 and other embodiments as described below systemize regimens that include one or more of these components, reducing some costs or risks associated with a haphazard or generic regimen. After a start operation, operational flow 100 moves to operation 130, comprising receiving a test result of a state of a subject. In some instances, the test result may be a verbal description (such as "healthy"), an outcome such as a success, or other information describing, measuring, or reported about the state of a subject.

Flow 100 then moves to operation 150, comprising indicating an amount of a nutraceutical partly based on the test result and partly based on a regimen, and to an end operation. The digital indication can be a display or other transmission, for example. FIGS. 7-14 below include many variations of operational flow 100. In various embodiments such as these, of course, flow 100 can include additional operations or variations in the sequence of operations.

Referring now to FIG. 2, there is shown an example system 200 in schematic form, a hardware implementation able to perform variants of flow 100 as described below. Primary module 210 includes circuitry 230 for receiving a test result (as a part of input 232, e.g.) of a state of a subject (an animal or other organism, e.g.). Primary module 210 further includes logic 240 (such as a processor or programmable logic, e.g.) for digitally indicating an amount of a nutraceutical (as output 238, e.g.) partly based on the test result and partly based on a regimen. Primary module 210 can further include medium 250 accessible by at least logic 240, as described below. (The dashed outline of medium 250 signifies that some embodiments are specifically contemplated to exclude this feature, and others are contemplated to include it.)

Input 232 can include one or more of analog data, digital data, or a measurable physical property such as a distance or similar geometry. Alternatively or additionally, input 232 can comprise a conduit bearing one or more instructions that can be stored in medium 250, for example, or can be executed by logic 240 to perform one or more variations of flow 100 such as those shown in FIGS. 7-14. Alternatively or additionally, circuitry 230 can optionally receive information (such as the regimen, e.g.) remotely, via input 232.

Referring now to FIG. 3, there is shown another example system 300 able to perform operational flow 100 of FIG. 1 and many similar variations. System 300 includes circuitry 330 and logic 340 as described below, and can further include one or more of link 333, link 338, or medium 350. Logic 340 can optionally receive input from a user (such as from user 360 via link 338, e.g.) locally. Medium 350 can bear one or more instructions that can be executed by logic 340 (optionally a processor, e.g.) for performing any of the flows of FIGS. 7-14.

As shown, link 333 can operably couple system 300 with network 320. In some embodiments, network 320 can thus have access to online research resource 312 through linkage 322 or to server 313 through linkage 323. Alternatively or additionally, network 320 can have access to expert 314 through linkage 324 or to test site 380 through linkage 381. Research resource 312 can be remote from system 300 or from server 313, expert 314, or test site 380. Expert 314 can optionally be located at a clinic or similar retail or healthcare facility that can advantageously include system 300 as well as one or more of online research resource 312, server 313, test site 380, or user 360.

In some embodiments, test site 380 includes one or more of sensor 385, sample 386, or reagent 387. System 300 optionally includes circuitry (optionally circuitry 330 with link 333, e.g.) for communicating with test site 380 via network 320, such as by electronic mail, facsimile, or a similar digital format. Alternatively or additionally, circuitry 330 can coordinate with link 333 for communicating with a regimen server (such as server 313, e.g.) or with a consultant (such as expert 314) remotely. Alternatively or additionally, test site 380 can be configured to communicate with expert 314 via linkage 382 or with (another) user 360 via linkage 362.

Referring now to FIG. 4, there is shown another example system 400 able to perform operational flow 100 of FIG. 1 and many similar variations such as thos of FIGS. 7-14. System 400 includes circuitry 430 and logic 440 as described below, and can further include one or more of link 432, link 433, link 438, link 495, or medium 450. Logic 440 can optionally include link 438 configured as a display or similar user interface for communicating locally with a user (such as with user 460, e.g.). Alternatively or additionally, module 410 can optionally include a display medium (such as a printable prescription, e.g.) configured for indicating the amount of the nutraceutical digitally.

As shown, system 400 also integrates a test site 480 that can include a sensor 485 and/or a sample 486. Test site 480 can be configured to receive one or more fluid samples (such as a blood sample, a saliva sample, or a urine sample from the subject, e.g.). Alternatively or additionally test site 480 can be configured to receive a hair sample, a skin sample, or the like as sample 486 from the subject for which the test result is obtained. Sensor 485 can be made operable for obtaining the test result adjacent to sample 486 via linkage 462 as shown, for example.

Logic 440 can be operable to receive input from or send output to inventory manager 490, for example, in lieu of receiving inventory information via a network or a user. Inventory manager comprises a regimen component $C_1$ 491 comprising a nutraceutical and optionally comprising one or more other regimen components $C_2$ 492. Of course it is specifically contemplated system 400 can be configured to operate without a direct link 495 to any inventory manager, or that inventory manager 490 can be accessible to user 460 (as indicated by linkage 469). Alternatively, circuitry 430 and link 433 can be configured for communicating to inventory manager 490 (via linkage 425 through network 420, e.g.). In this way, inventory manager 490 can be remote from user 460, for example in an implementation by which the components 491, 492 are periodically or occasionally shipped to user 460 from a remote location.

Referring now to FIG. 5, there is shown another example system 500 able to perform operational flow 100 of FIG. 1 and many similar variations. System 500 includes module 530 for digitally indicating (via output 522, e.g.) an amount of a nutraceutical partly based on a result of a test of a state of a remote subject and partly based on a regimen. Module 530 at least partly overlaps with circuitry 550 for receiving the test result, such as via input 521 from network 520 that can include, for example, the entirety of FIG. 4. Alternatively or additionally, server 313 of FIG. 3 can be configured as system 500, coupling through linkage 323 configured to include both input 521 and output 522.

As shown, module 530 can optionally include one or more of processor 534, logic 536, or logic 538. Circuitry 550 can optionally include one or more of logic 554, logic 556, or memory 558. Storage 560 can optionally include one or more of code 566, historical data 568, or other data 570 such as one or more regimens 572, 574.

In some embodiments, logic 554 can comprise logic for prompting the test result by requesting a test that partly depends on a medical history of the subject, for example, by transmitting a prompting signal as output 522 to network 520. (See FIG. 7.) Alternatively or additionally, for example, logic 556 can comprise logic for receiving an indication that the subject consumed at least the amount of the nutraceutical, and optionally logic for interpreting the indication. (See FIG. 11.)

In some embodiments, logic 556 instead comprises logic for storing at least a portion of the regimen locally before receiving the test result, such as by receiving the portion of the regimen via input 521 into memory 558 and storing the portion as a regimen 572 of data 570. (The remainder may, of course, be received later and also stored in regimen 572.) Such a received (partial or complete) regimen is then available for retrieval, for example, responsive to a download request or a test result received as input 521.

When a test result is so received, logic 536 can optionally respond by storing the test result with other medical history data of the subject, such as in historical data 568. (See FIG. 7) Historical data 568 can also include one or more test results from one or more other subjects, optionally from a common population to which the subject belongs.

Referring now to FIG. 6, there is shown a system 600 including at least a signal-bearing medium 610 that can optionally comprise one or more of conduit 620, disk 630, integrated circuit 640, or processor 650. Signal bearing medium can optionally bear one or more of several instruction sets as shown that system 600 can use for performing flow 100. Alternatively or additionally, system 600 can be a computer program product for enabling a system 200 of FIG. 2, system 300 of FIG. 3, system 400 of FIG. 4, or system 500 of FIG. 5 to perform flow 100 when executed. For example, signal-bearing medium 610 may be an integrated circuit 640 bearing one or more instructions 660 that when executed by processor 650 cause system 600 to perform at least one of (a) receiving a test result of a state of a subject and (b) indicating an amount of a nutraceutical partly based on the test result and partly based on a regimen.

Medium 610 can optionally include one or more instructions 661 for prompting the test result by requesting a test that partly depends on a medical history of the subject (referring to those of operation 130, of course.) Alternatively or additionally, medium 610 can likewise include one or more instructions 664 for applying to the test result one or more criteria at least partly based on one or more other test results of the subject. Alternatively or additionally, medium 610 can likewise include one or more instructions 665 for transmitting an indication of the state of the subject through a network. Alternatively or additionally, medium 610 can likewise include one or more instructions 668 for storing the test result with other medical history data of the subject. Alternatively or additionally, medium 610 can likewise include one or more instructions 674 for selecting the amount of the nutraceutical partly based on a medical history of the subject. Alternatively or additionally, medium 610 can likewise include one or more instructions 676 for determining the amount of the nutraceutical responsive to test data from one or more other members of a population that includes the subject. Alternatively or additionally, medium 610 can likewise include one or more instructions for receiving an indication of a nominal quantity of the nutraceutical within each of one or more delivery units and one or more instructions for indicating the amount of the nutraceutical as a number of the one or more delivery units 678.

In some embodiments, one or more signal-bearing media comprise disk 630 accessible to integrated circuit 640, which is configured to retrieve and execute one or more of the instruction(s) 661-678 from disk 630.

Figure 7:
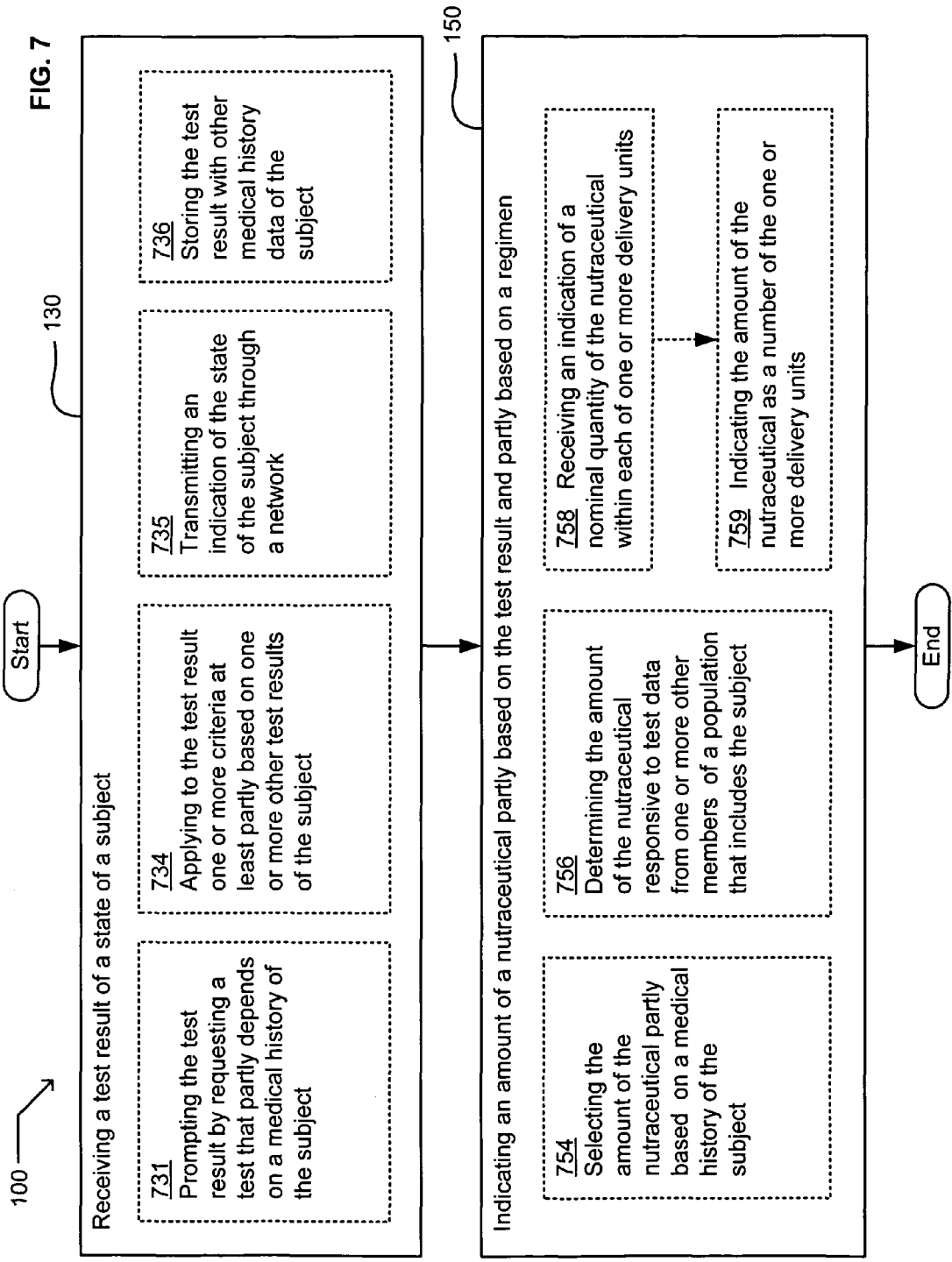
FIG. 7 shows various optional features of the flow of FIG. 1.

Referring now to FIG. 7, there are shown various optional features of operational flow 100 of FIG. 1. Except as noted, circuitry 330 and logic 340 can optionally perform one or more of operation 731, operation 734, operation 735, or operation 736 in respective variations of receiving operation 130. Also logic 340 and link 338 can optionally perform one or more of operation 754, operation 756, operation 758, or operation 759 in respective variations of indicating operation 150. Any of these additional operations can provide unexpected enhancements in health management when performed in contexts like those of FIGS. 2-6.

Optional operation 731 comprises prompting the test result by requesting a test that partly depends on a medical history of the subject. Medium 350 can optionally contain a full or partial medical history of a woman (user 360, e.g.) having an interest in adding bee products into her supplement regimen, for example. Alternatively or additionally, part or all of the medical history may be obtained via link 333 and/or link 338. Logic 340 can determine whether her retrieved history shows a strong reaction to pollen and can, depending on the implemented health regimen, prompt her to consider taking an allergy and/or pregnancy test before changing her regimen. If she decides not to perform either test but to proceed with some risk, logic 340 can prompt her to consume small amounts during the first few days of taking the supplement.

In an alternative embodiment, a physician or other health care provider can personally review a medical history and draw upon his/her expertise to decide upon a test that will or might be needed in the event of some contingency such as an infection, an injury, or a specific symptom (weight loss or fever, e.g.). The care provider can improve his/her effectiveness at a next visit by having the patient (user 360, e.g.) receive a prompting (by operation 731, e.g.) to initiate the test before the office visit. And the test result may also prompt logic 340 to indicate a safe supplement regimen for the patient to begin immediately (at operation 150, e.g.), even before the next visit.

Any of the systems of FIGS. 2-5 can likewise perform operation 731 in a variant of flow 100 by including the one or more instructions 661 (of FIG. 6) for prompting the test result by requesting a test that partly depends on a medical history of the subject.

Optional operation 734 comprises applying to the test result one or more criteria at least partly based on one or more other test results of the subject. The one or more criteria may constitute a diagnosis, for example, based on the other test result(s). The result of operation 734 can include one or more of referring the subject to a health care provider, asking about the subject's compliance with the regimen, asking one or more other questions, prompting the subject to undergo further testing (by repeating operation 731, e.g.), downloading a condition-specific regimen associated with the one or more other test results, or proposing another nutraceutical or medication.

Any of the systems of FIGS. 2-5 can likewise perform operation 734 in a variant of flow 100 by including the one or more instructions 664 (of FIG. 6) for applying to the test result one or more criteria at least partly based on one or more other test results of the subject.

Optional operation 735 comprises transmitting an indication of the state of the subject through a network. The indication may be transmitted to one or more of a body of research resource 312, a server 313, an expert 314, or a test site 380. The indication can optionally depend on the test result, can include the test result, and/or can include other information about the subject. The indication can be anonymous or can include detailed information about the subject and the subject's family. The indication can comprise a prompting to conduct the test resulting in the test result (by operation 731, e.g.). The indication can determine or be used in deciding which test(s) to perform, when, in what order, and with what contingent responses. The indication can optionally determine a message destination (such as a specialist) that depends on the state of the subject.

Any of the systems of FIGS. 2-5 can likewise perform operation 735 in a variant of flow 100 by including the one or more instructions 665 (of FIG. 6) for transmitting an indication of the state of the subject through a network.

Optional operation 736 comprises storing the test result with other medical history data of the subject. Logic 340 may accumulate such test results in medium 350, for example. Later it can be used e.g., for aggregation at a server 313 having analogous results from other subjects and/or other data from/about the subject (user 360, e.g.). Alternatively or additionally the stored result can be used by logic 340 in performing operation 754 of selecting the amount of the nutraceutical partly based on a medical history of the subject. The medical history can include any combination of data from a comprehensive digital record to a mere fact (such as the subject's current age or weight).

Any of the systems of FIGS. 2-5 can likewise perform operation 736 in a variant of flow 100 by including the one or more instructions 668 (of FIG. 6) for storing the test result with other medical history data of the subject.

In another variant including operation 754, a mother (user 360, e.g.) performs a blood test for the subject (her child) using a test site 380 at their home. She applies the sample 386 to a reagent 387 (test strip, e.g.) and obtains the result visually. System 300 (a computer, e.g.) receives the test result via link 338 and transmits it via network 320. Server 313 receives the test result via linkage 323 and applies an expert's regimen to generate a consumption regimen that is transmitted (by operation 735, e.g.) to system 300, which displays the child's (proposed) regimen to the mother. In this example, system 300 can perform flow 100 with operation 735, for example, optionally using an ordinary web browser interface. Also server 313 performs a variant of flow 100 that includes operation 754. Optionally the server 313 can include additional operations such as storing operation 736.

Any of the systems of FIGS. 2-5 can likewise perform operation 754 in a variant of flow 100 by including the one or more instructions 674 (of FIG. 6) for selecting the amount of the nutraceutical partly based on a medical history of the subject.

Alternatively or additionally, server 313 can perform flow 100 so as to include operation 756 of determining the amount of the nutraceutical responsive to test data from one or more other members of a population that includes the subject.

There is widespread interest in the efficacy of nutraceuticals in general and also in specific populations (such as children, e.g.). A study can facilitate participation using a variant of flow 100 in which testing is non-intrusive (by tracking a blood pressure, a temperature, a body weight, a duration, or a saliva content, e.g.), in which privacy is assured (by anonymity or password protection, e.g.), and/or in which remote participation is encouraged (by operation 735, e.g.).

Any of the systems of FIGS. 2-5 can likewise perform operation 756 in a variant of flow 100 by including the one or more instructions 676 (of FIG. 6) for determining the amount of the nutraceutical responsive to test data from one or more other members of a population that includes the subject.

Optional operation 758 comprises receiving an indication of a nominal quantity of the nutraceutical within each of one or more delivery units. The delivery units can be capsules, caplets, cans, drops, or the like, or defined combinations of these, e.g. They can contain a pure nutraceutical, a combination of nutraceuticals, one or more pharmaceuticals, or cups or similar vessels used for handling these dispensations. Optional operation 759 comprises indicating the amount of the nutraceutical as a number of the one or more delivery units. Logic 340 can perform this operation, for example, and then physically dispense the indicated amount(s) with great accuracy.

Any of the systems of FIGS. 2-5 can likewise perform operation 758 or operation 759 in a variant of flow 100 by including the one or more instructions 678 (of FIG. 6) for receiving an indication of a nominal quantity of the nutraceutical within each of one or more delivery units or indicating the amount of the nutraceutical as a number of the one or more delivery units. Alternatively or additionally a display (link 338, e.g.) can perform operation 758 and operation 759. Rather than measuring out a powder by a volumetric standard, for example, user 360 (of FIG. 3) can count out the indicated integer number to achieve a high degree of dispensation accuracy.

Figure 8:
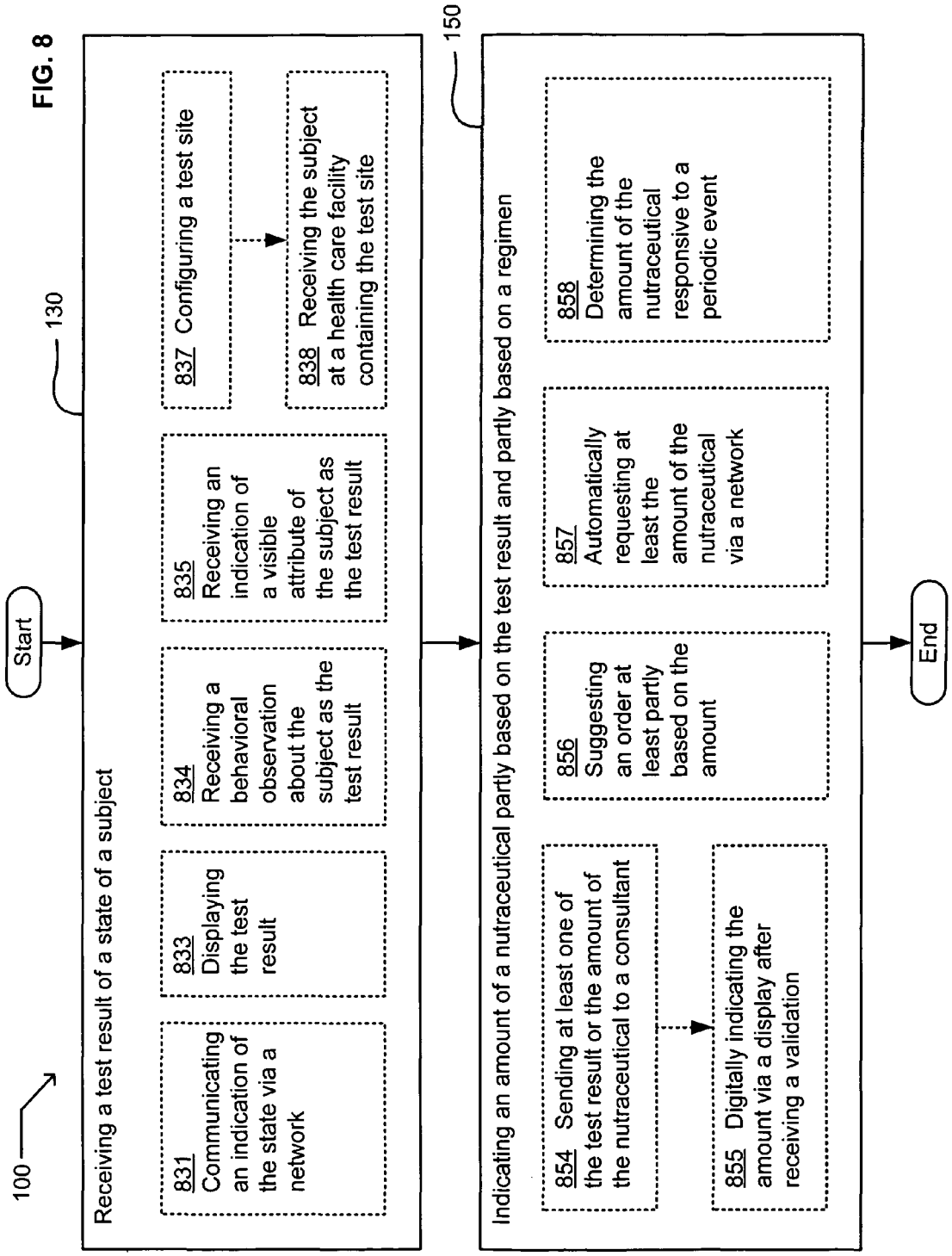
FIG. 8 shows additional variants of the flow of FIG. 1 or FIG. 7.

Referring now to FIG. 8, there are shown various optional features of operational flow 100 of FIG. 1. Except as noted, any of the systems 200, 300, 400, 500 of FIGS. 2-5 can optionally perform one or more of operation 831, operation 833, operation 834, operation 835, operation 837, or operation 838 in respective variations of receiving operation 130. Except as clearly dictated by context, any of them can likewise perform one or more of operation 854, operation 855, operation 856, operation 857, or operation 858 in respective variations of indicating operation 150. These additional operations can each provide unexpected enhancements in health management when performed in contexts like those of FIGS. 2-5.

Optional operation 831 comprises communicating an indication of the state via a network. The test result may include a subjective or objective, qualitative or quantitative, general or specific, implied or inferred, speculative or certain, past or present, transitory or other empirical result of a test of the state of the subject. Operation 831 can include communicating the indication to the network (such as by system 300 of FIG. 3, e.g.) or from the network (such as by system 500 of FIG. 5, e.g.). The indication is optionally communicated through one or more wireless links or via a signal-bearing medium 610 comprising a conduit 620.

Optional operation 833 comprises displaying the test result, for example by a direct linkage 462 (of FIG. 4) from a test site 480 or by an indirect linkage such as logic 440, implemented as a display to the subject or other user 460.

Optional operation 834 comprises receiving a behavioral observation about the subject as the test result, for example via input 232 (in an embodiment of system 200 of FIG. 2) from the subject, a psychologist, a psychiatrist, a parent, some other care provider, an instrument or other test apparatus, or some other observer. The observation may comprise an objective indication (conscious, e.g.) and/or a subjective indication (irritable or fatigued, e.g.). The observation can relate to past behavior ("slept poorly," e.g.) as well as present behavior.

Optional operation 835 comprises receiving an indication of a visible attribute of the subject as the test result, for example via input 232 (in an embodiment of system 200 of FIG. 2) from an instrument or other observer. The indication may relate to a facial attribute ("bags under the eyes," e.g.), some other skin condition ("rash," e.g.), or any other visible attribute of a subject. A message may be received via input 232, for example, including the indication and an identification of the observer. The message may, of course, include one or more other test results also.

Optional operation 837 comprises configuring a test site. This is optionally accomplished by configuring the test site in a portable system (as system 400, e.g.), optionally integral with a system that performs flow 100, or optionally within a facility of the subject such as a home.

Optional operation 838 comprises receiving the subject at a health care facility containing the test site. In performing flow 100 with operation 838, for example, system 400 can receive the subject by having test site 480 (a scale, e.g.) at a clinic at which the subject (user 460, e.g.) is receiving care.

Optional operation 854 comprises sending at least one of the test result or the amount of the nutraceutical to a consultant such as a physician, a pharmacist, a chiropractor, a nutritionist, or an insurance or other specialist. This can be performed by circuitry 330 of FIG. 3, for example, sending this information via link 333. Alternatively or additionally, logic 340 can perform operation 855 of digitally indicating the amount via a display after receiving a validation, such as a validation from or resulting from the consultant.

Optional operation 856 comprises suggesting an order at least partly based on the amount, such as by logic 440 of FIG. 4 displaying the suggested order for user 360 to consider or act upon. Alternatively or additionally, logic 440 can perform operation 857 of automatically requesting at least the amount of the nutraceutical via a network (such as network 420), such as by an online ordering or re-ordering process. The amount of the automatic request will typically be a one week supply or more.

Optional operation 858 comprises determining the amount of the nutraceutical responsive to a periodic event such as a daily event or other standard interval. The periodic event optionally determines the timing of the amount with substantially no influence on the value of the amount.

Figure 9:
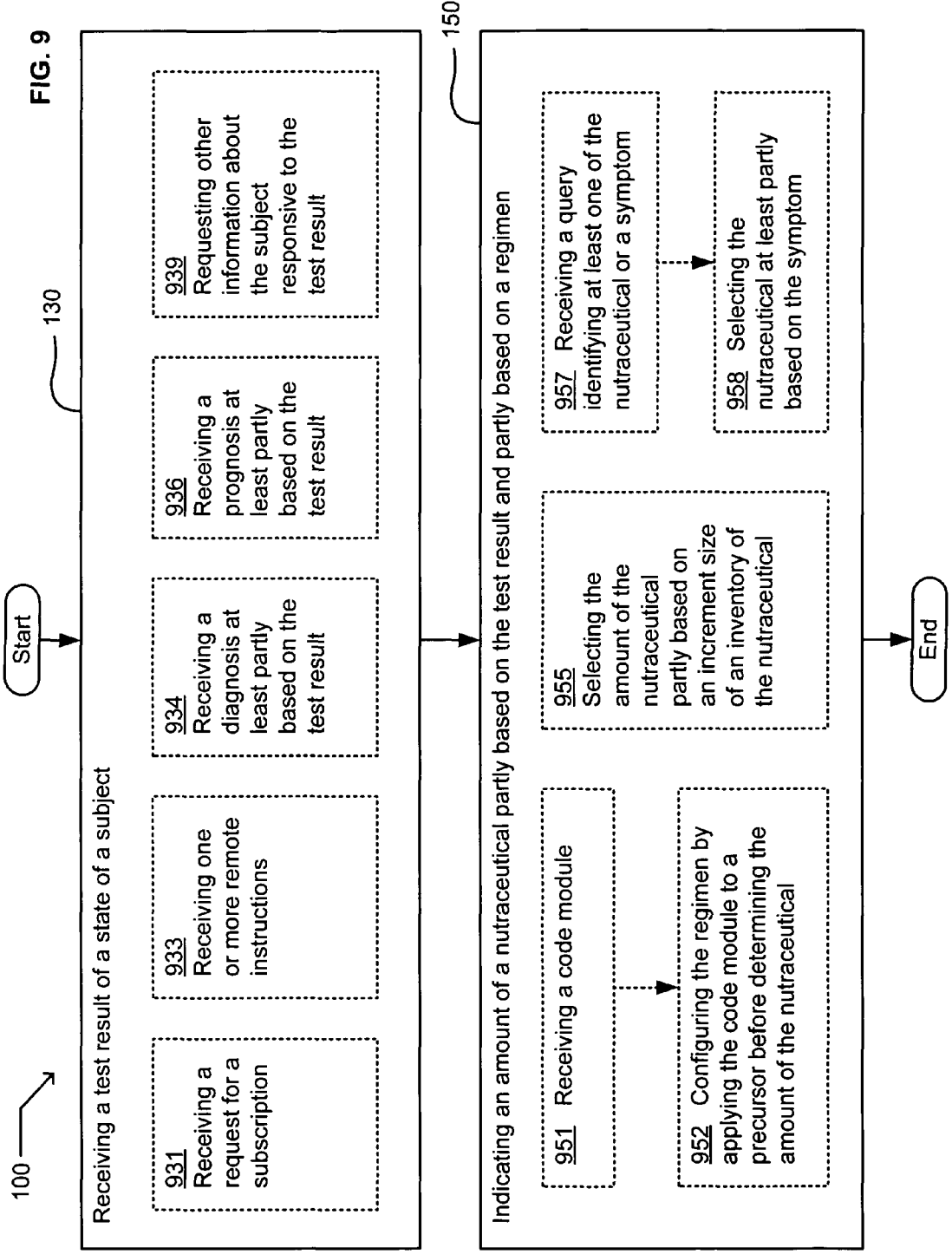
FIGS. 9-14 show further additional variants of the flow of FIG. 1, 7, or 8.

Referring now to FIG. 9, there are shown various optional features of operational flow 100 of FIG. 1 or FIG. 8. Circuitry 230 and logic 240 can optionally perform one or more of operation 931, operation 933, operation 934, operation 936, or operation 939 in respective variations of receiving operation 130, for example. Alternatively or additionally, logic 240 can perform one or more of operation 951, operation 952, operation 955, operation 957, or operation 958 in respective variations of indicating operation 150. Any of these additional operations can provide unexpected enhancements in health management.

Optional operation 931 comprises receiving a request for a subscription. An accomplished celebrity or recognized expert in the field of diet or nutrition, for example, may disseminate a regimen incorporating one or more nutraceuticals to a population of subscribers using the present embodiment. Alternatively or additionally, as described above, system 200 can be a server configured to perform the herein-described variants of flow 100 for efficiently aggregating data for primary research upon hundreds or thousands of subscribers to demonstrate, contraindicate, or improve the efficacy of a nutraceutical or a regimen for a given purpose. Additionally or alternatively, system 200 can optionally grant, sell, or otherwise facilitate subsriptions for the regimen online before beginning, completing, or repeating the indicating operation 150.

Optional operation 933 comprises receiving one or more remote instructions. In a system 200 that includes a module for indicating an amount of a nutraceutical partly based on the test result and partly based on a regimen (logic 240, e.g.), this component is readily implemented in a hand-held device or a computer, for example. System 200 can further include circuitry 230 for receiving a test result of a state of a subject and for receiving one or more remote instructions. This circuitry 230 can receive the test result and remote instruction(s) as input 232.

In some embodiments, input 232 can include other items. Input 232 and medium 250 can each include one or more components of the regimen. Optional operation 934 comprises receiving a diagnosis at least partly based on the test result, optionally as input 232 to circuitry 230. Optional operation 936 comprises receiving a prognosis at least partly based on the test result, alternatively or additionally, as input 232 to circuitry 230. The diagnoses and/or prognoses are optionally accompanied by one or more references to a person or a document that the user can access for further information.

Optional operation 939 comprises requesting other information about the subject responsive to the test result. This can include requesting other information about a future event (as described at operation 831, e.g.) or a past event (as described at operation 834, e.g.). Alternatively or additionally, it can include requesting a genetic attribute such as gender or blood type, a subjective circumstance such as a comfort level or an interest level, an age, a general category such as a fitness or activity level, or any other subject attributes of therapeutic or correlative relevance.

Optional operation 951 comprises receiving a code module, such as via circuitry 230. The code module can include one or more data items describing the subject or the test result, for example, or one or more executable instructions for obtaining or using such a data item. One way to use such a code module is for logic 240 to perform operation 952 which comprises configuring the regimen by applying the code module to a precursor before determining the amount of the nutraceutical. Optional operation 952 can be used to initiate, maintain, modify, or otherwise update a local representation of the regimen.

Optional operation 955 comprises selecting the amount of the nutraceutical partly based on an increment size of an inventory of the nutraceutical. An increment size is desirably selected as about 2% to 20% of a maximum daily value of the amount of the nutraceutical based on the regimen. The percentage is desirably selected as a higher percentage for nutraceuticals that are inexpensive or intended for manual dispensation.

Optional operation 957 comprises receiving a query identifying at least one of the nutraceutical or a symptom. Logic 240 can optionally use this information for selecting the nutraceutical (or a suitable substitute) or to interact with a user to determine a motivation for the query. If the received query identifies a symptom, logic 240 can optionally or conditionally perform operation 958 of selecting the nutraceutical at least partly based on the symptom.

Figure 10:
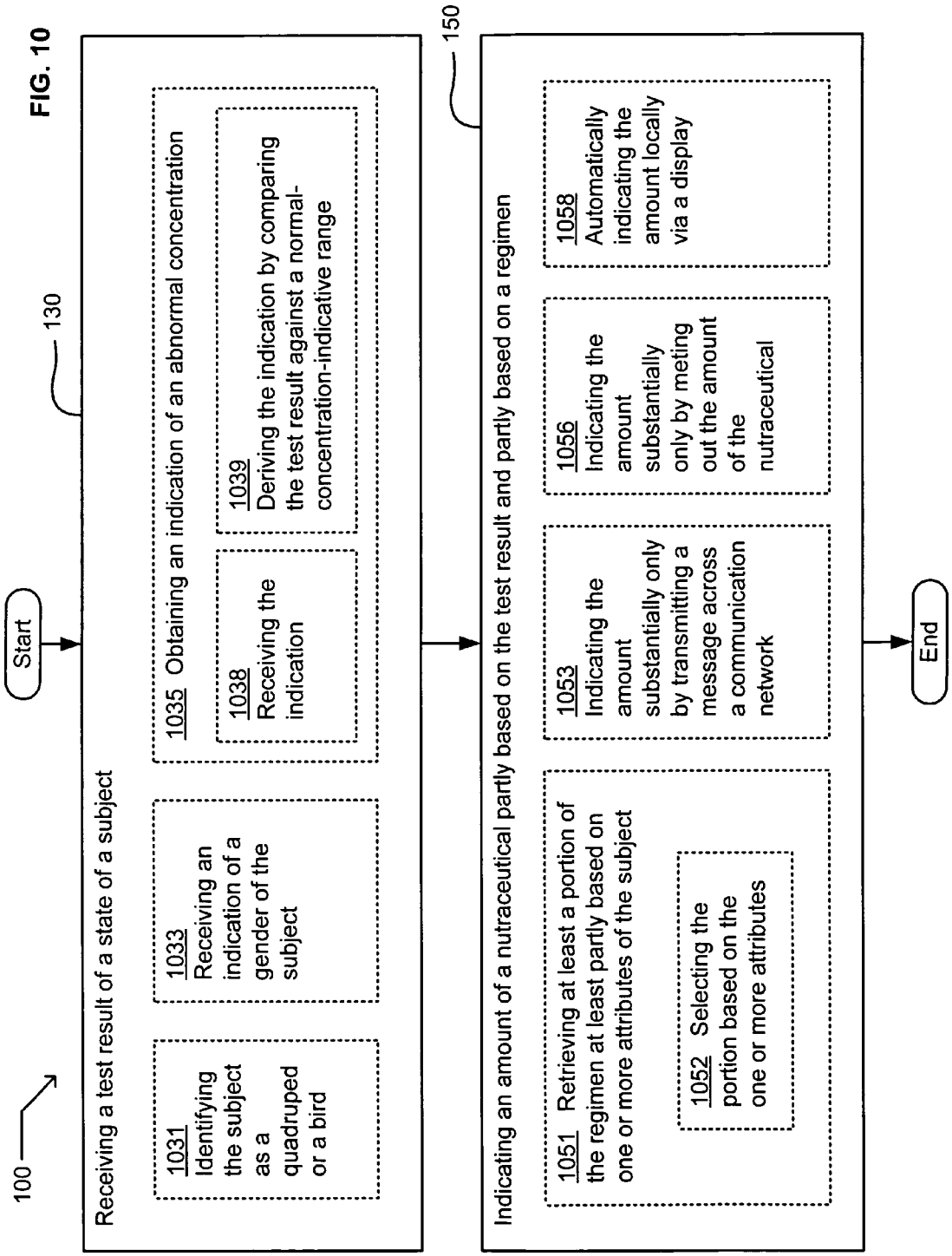

Referring now to FIG. 10, there are shown various optional features of operational flow 100 of FIG. 1, 8, or 9. Circuitry 230 and logic 240 can optionally perform one or more of operation 1031, operation 1033, operation 1035, operation 1038, or operation 1039 in respective variations of receiving operation 130, for example. Alternatively or additionally, logic 240 can perform one or more of operation 1051, operation 1052, operation 1053, operation 1056, or operation 1058 in respective variations of indicating operation 150. Any of these additional operations can provide unexpected enhancements in health management.

Various embodiments of the present invention can be very useful in managing the health of animals with dispensations that include a nutraceutical. For example, optional operation 1031 comprises identifying the subject as a quadruped or a bird. Alternatively or additionally, logic 240 can perform operation 1033 of receiving an indication of a gender of the subject. System 200 can be set up, for example, in a clinic that allows for such indications to be received from a user with access to an inventory manager stocking a wide variety of medications and supplements like the configuration of FIG. 4.

In various embodiments, receiving a test result can include receiving at least one of a decision or other result of one or more applied criteria, a direct reading, a qualitative evaluation, an estimate, an error indication, a physical quantity, or some similar expression. Optional operation 1035 comprises obtaining an indication of an abnormal concentration, as one example. One way such an indication can be obtained is by operation 1038 of receiving the indication. Another is by operation 1039 of deriving the indication by comparing the test result against a normal-concentration-indicative range or by applying one or more other criteria to the test result.

Optional operation 1051 comprises retrieving at least a portion of the regimen at least partly based on one or more attributes of the subject. In some embodiments, in which system 200 is a server for example, a large number of regimens can be stored in one or more media 250. Operation 1051 can be performed, in this case, at least partly based on an attribute such as age, weight, ethnicity, blood type, preference, goal, or a name or a similar individual or group identifier, or some combination of attributes like these.

In some embodiments, optional operation 1051 can be performed merely by operation 1052 of selecting the portion based on the one or more attributes. In others, the regimen itself is derived at least partly based on one or more attributes of the subject. In cases like these, medium 250 can be configured especially for just one subject, substantially containing data for just one regimen, significantly reducing the resources needed for a given level of refinement.

Optional operation 1053 comprises indicating the amount substantially only by transmitting a message across a communication network, neither archiving nor displaying the amount locally. This method may be preferred for configurations of system 200 in which (nonvolatile) storage is limited, for example, or where the amount is primarily intended for use by a remote supplier.

Optional operation 1056 comprises indicating the amount substantially only by meting out the amount of the nutraceutical. Such a meting out can optionally be performed by an inventory manager like a vending machine, containing "unit dose" packages arranged in carriers each large enough to contain the required components. An inventory manager can alternatively be implemented very simply (in bottles, e.g.) and used in coordination with logic 240 configured to perform operation 1058 of automatically indicating the amount locally via a display. Primary module 210 can even be implemented in a wrist watch or similar hand-held device.

Figure 11:
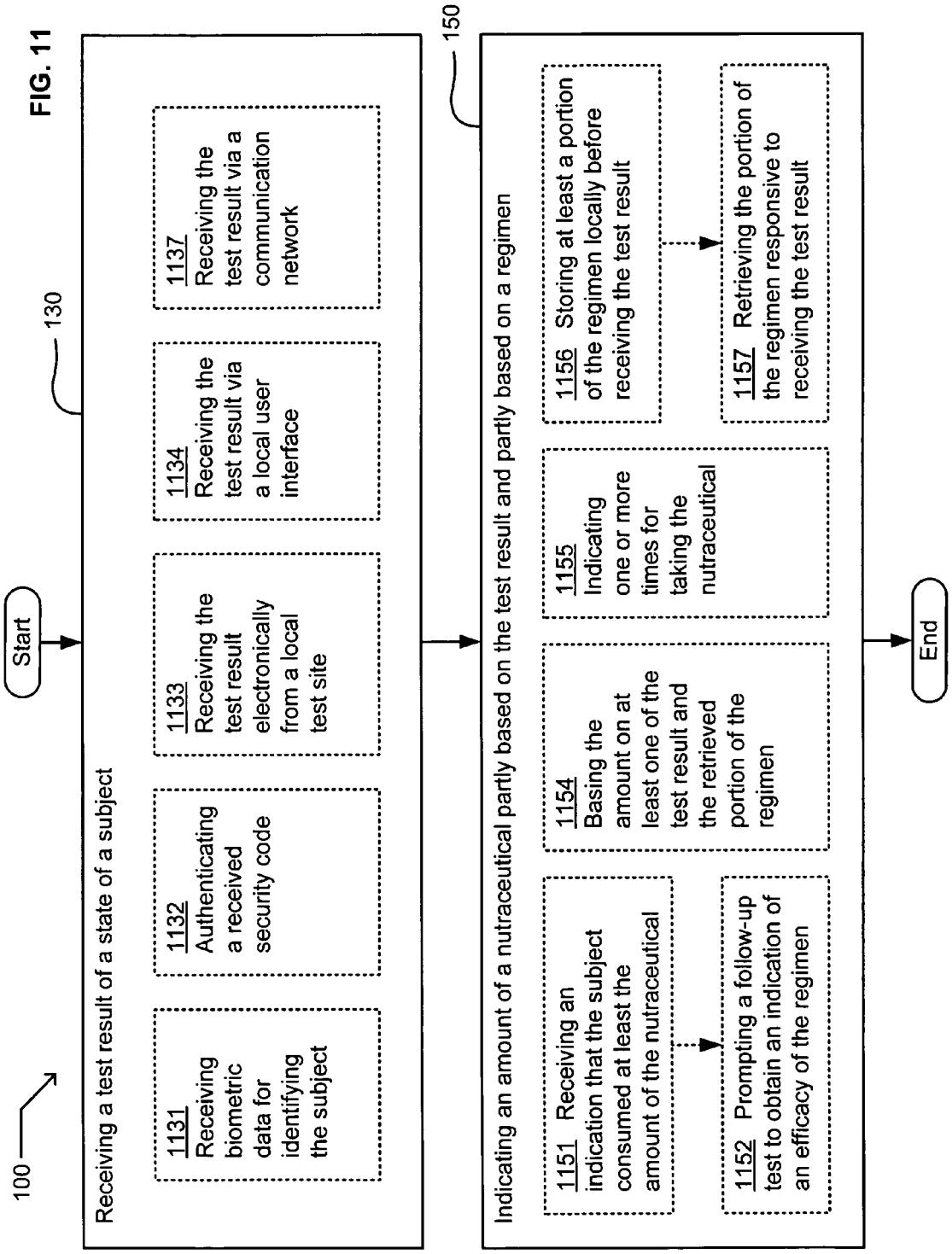

Referring now to FIG. 11, there are shown various optional features of operational flow 100 of FIG. 1, 8, 9, or 10. Circuitry 430 and logic 440 can optionally perform one or more of operation 1131, operation 1132, operation 1133, operation 1134, or operation 1137 in respective variations of receiving operation 130, for example. Alternatively or additionally, logic 440 can perform one or more of operation 1151, operation 1152, operation 1154, operation 1155, operation 1156, or operation 1157 in respective variations of indicating operation 150. Any of these additional operations can provide unexpected enhancements in health management.

Optional operation 1131 comprises receiving biometric data for identifying the subject. The biometric data can include an image such as a fingerprint or retinal scan, timing biometrics such as a heartbeat or a voice, behavioral biometrics such as a signature, or the like. Alternatively or additionally, the integrity of system 400 can be secured by performing operation 1132 of authenticating a received security code, such as for authenticating the test result or a received instruction (at operation 933, e.g.).

Optional operation 1133 comprises receiving the test result electronically from a local test site. The test site 480 can be integral with the system 400, for example, or otherwise accessible within a vicinity via a local link 432. Link 432 can include a signal-bearing conduit, or can include a Bluetooth™ or other short range wireless link.

Optional operation 1134 comprises receiving the test result via a local user interface. Irrespective of link 432, for example, logic 440 can receive the test result via link 438, which can be a local user interface. Alternatively or additionally, logic 440 can perform operation 1137 of receiving the test result via a communication network. The communication network can be LAN comprising link 432, for example, or a WAN such as in a configuration like that of FIG. 3.

Optional operation 1151 comprises receiving an indication that the subject consumed at least the amount of the nutraceutical. Such an indication is optionally used for updating an electronic inventory in medium 450, for example, or transmitted via link 333. The indication can be received via link 438, for example, in response to a message asking the user whether the subject consumed one or more components of the regimen.

The indication is optionally received intermittently (on a sampled basis, e.g.) or otherwise in a manner that is not contemporaneous with each dispensation of a regimen. Alternatively or additionally, logic 440 prompts user 460 for other real-world status information. Logic 440 can perform operation 1152, for example, of prompting a follow-up test to obtain an indication of an efficacy of the regimen.

In some embodiments, part or all of the regimen is retrieved. Optional operation 1154 comprises basing the amount on at least one of the test result and the retrieved portion of the regimen, for example.

Some embodiments allow for a dispensation or consumption that can be remote from system 400. Optional operation 1155 comprises indicating one or more times for taking the nutraceutical, for example by an interface such as link 438. This allows for an intentional lapse before a dispensation or a consumption of a dispensation, which can be helpful for facilitating travel or for implementing a regimen with more than one scheduled consumption per day.

Optional operation 1156 comprises storing at least a portion of the regimen locally before receiving the test result. Alternatively the system 400 can be obtained with substantially all of the regimen already installed. Alternatively or additionally a system (such as system 300) may perform the receiving operation 130 by passing the test result along to a network (such as network 320) that responds by providing the information needed for the system to perform operation 150. If system 400 has access to at least some of the regimen, system 400 can optionally perform operation 1157 of retrieving the portion of the regimen responsive to receiving the test result.

Figure 12:
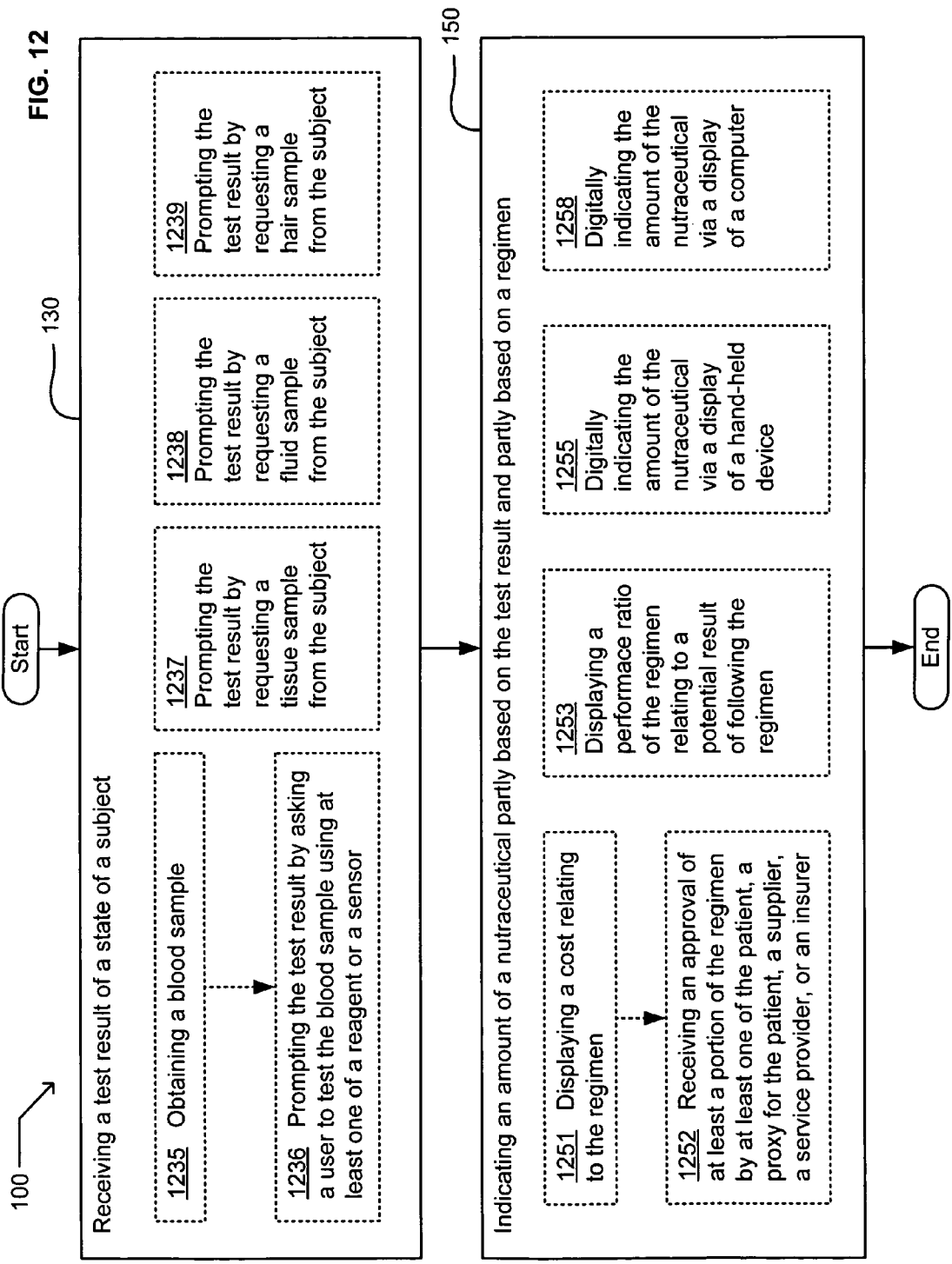

Referring now to FIG. 12, there are shown various optional features of operational flow 100 of FIG. 1, 8, 9, 10, or 11. Circuitry 330 and logic 340 can optionally perform one or more of operation 1235, operation 1236, operation 1237, operation 1238, or operation 1239 in respective variations of receiving operation 130, for example. Alternatively or additionally, logic 440 can perform one or more of operation 1251, operation 1252, operation 1253, operation 1255, or operation 1258 in respective variations of indicating operation 150. Any of these additional operations can provide unexpected enhancements in health management.

Optional operation 1235 comprises obtaining a blood sample. Test site 380 can optionally be implemented conventionally at a care provider facility or at a laboratory to which the blood sample is sent. Test site 380 can alternatively be implemented at a location local to the subject, with the sensor 385 and/or reagent 387 optionally used locally. For a test initiation substantially contemporaneous with the obtaining the blood sample, for example, logic 340 can perform operation 1236 of prompting the test result by asking a user to test the blood sample using at least one of a reagent or a sensor.

Of course testing on other fluids and tissue types and other testing can be used with or as an alternative to obtaining the blood samples. System 300 can facilitate these, for example, by prompting the test result by requesting a tissue sample from the subject (at operation 1237, e.g.), by requesting a fluid sample from the subject (at operation 1238, e.g.), or by requesting a hair sample from the subject (at operation 1239, e.g.). Logic 340 or test site 380 can perform one or more of these operations, for example.

Optional operation 1251 comprises displaying a cost relating to the regimen. The cost can optionally be conditional, partial, or neither of these. The cost may be effectively negative, such as a discount or other incentive for a subject to participate in a trial regimen. The cost may be expressed in points or other non-monetary units. Logic 340 can optionally perform displaying operation 1251, for example, and may alternatively or additionally perform operation 1252 of receiving an approval of at least a portion of the regimen by at least one of the patient, a proxy for the patient, a supplier, a service provider, or an insurer.

Optional operation 1253 comprises displaying a performance ratio of the regimen relating to a potential result of following the regimen. The potential outcome can be tangible, intangible, subjective, objective, or some combination of these. The ratio can be an estimated probability of a measurable improvement, for example, or a ratio of "satisfied" regimen subscribers to "dissatisfied" regimen subscribers.

Operation 1255 comprises digitally indicating the amount of the nutraceutical via a display of a hand-held device, and operation 1258 comprises digitally indicating the amount of the nutraceutical via a display of a computer. The amount(s) may be expressed in terms of weight, volume, count, or other units of measure, or some combination of these.

Figure 13:
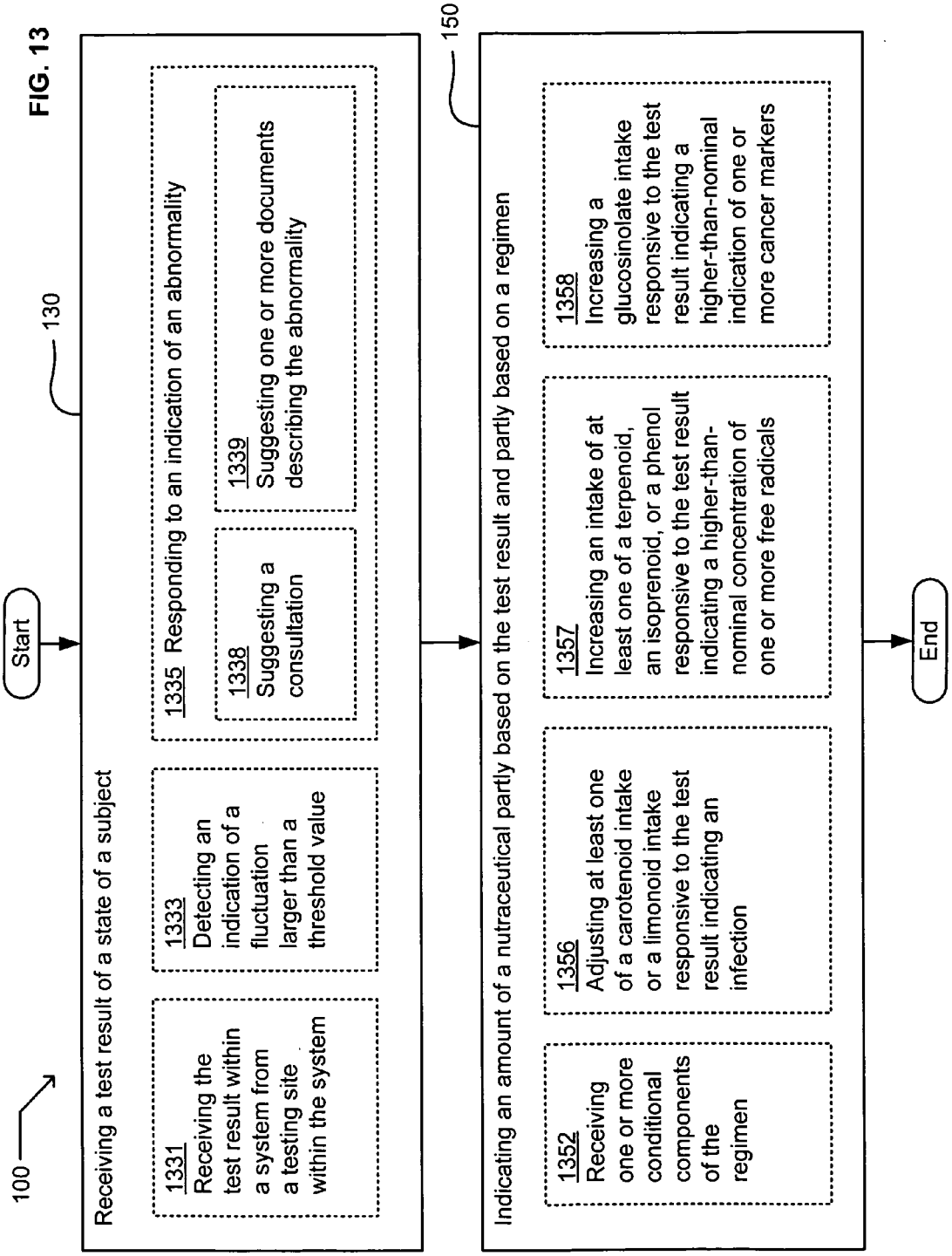

Referring now to FIG. 13, there are shown various optional features of operational flow 100 of FIG. 1, 8, 9, 10, 11, or 12. Circuitry 430 and logic 440 can optionally perform one or more of operation 1331, operation 1333, operation 1335, operation 1338, or operation 1339 in respective variations of receiving operation 130, for example. Alternatively or additionally, logic 440 can perform one or more of operation 1352, operation 1356, operation 1357, or operation 1358 in respective variations of indicating operation 150. Any of these additional operations can provide unexpected enhancements in health management.

Optional operation 1331 comprises receiving the test result within a system from a testing site within the system within receiving operation 130. Circuitry 430 can perform this action, for example, when receiving a test result from test site 480.

Optional operation 1333 comprises detecting an indication of a fluctuation larger than a threshold value within receiving operation 130. The presence, absence, sufficiency, or degree of fluctuation can be the test result, for example, or the fluctuation can be detected in a monitored signal such as by a transition between successive values of the test result.

Optional operation 1335 comprises responding to an indication of an abnormality. One or more criteria can be applied to distinguish between any of one or more "normal" indications and any of one or more abnormalities. Abnormalities may include any discovery of an illness, injury, allergy, or other mental or physical condition of potential or actual significance to a subject's health. For a larger expected or potential risk or need, system 400 can include logic 440 for suggesting a consultation (by operation 1338, e.g.). For any expected or potential risk or need identified, system 400 can include logic 440 for suggesting one or more documents describing the abnormality (by operation 1339, e.g.), such as by a hyperlink or similar annotation.

Optional operation 1352 comprises receiving one or more conditional components of the regimen, such as a function (with the test result as at least one of the arguments) that defines how much of the nutraceutical or other regimen components to indicate. The conditional components can comprise a markup language function definition, for example, or one or more computations that can be implemented with logic, firmware, software, etc.

Almost any specific nutraceutical with a perceived benefit can lead to an unexpectedly beneficial implementation by embodiments herein. For example, suppose that a care provider, a health columnist, or a person with a sick pet would like to try a carotenoid or limonoid to combat an infection in a specific subject. In some embodiments, rather than a layperson just trying some generic amount for a while, system 200 is configured to perform a variant of flow 100 that includes operation 1356. Operation 1356 comprises adjusting at least one of a carotenoid intake or a limonoid intake responsive to the test result indicating an infection. The test result may be an abnormally high concentration count of one or more white blood cells, a higher-than-nominal body temperature measurement, or some other indication suggesting the infection. The nominal value or range for the body temperature or other variable may be established relative to a published value or range for the subject. One or more criteria can also be adopted that take into account one or more attributes of the subject such as species, gender, age, state of exertion, state of sleep, state of pregnancy, state of hypothermia, or the like. Alternatively or additionally, one or more thresholds may be updated based on one or more prior measurements of the same subject, establishing an individualized nominal value or other definition of normality or abnormality.

Operation 1356 may comprise increasing the intake for several days, for example, responsive to the test result indicating a persistent infection. A later iteration of operation 1356 may comprise adjusting the intake to zero, for example, responsive to the test result indicating an infection that is not significantly affected by the regimen. This can optionally lead to a programmatic addition or substitution of one or more other supplements or medications to address the infection.

Similarly, system 200 can perform optional operation 1357 comprising increasing an intake of at least one of a terpenoid, an isoprenoid, or a phenol responsive to the test result indicating a higher-than-nominal concentration of one or more free radicals. Alternatively or additionally, system 200 can perform operation 1358 of increasing a glucosinolate intake responsive to the test result indicating a higher-than-nominal indication of one or more cancer markers. The intake, in these cases, can comprise a suggestion or other regimen component.

Figure 14:
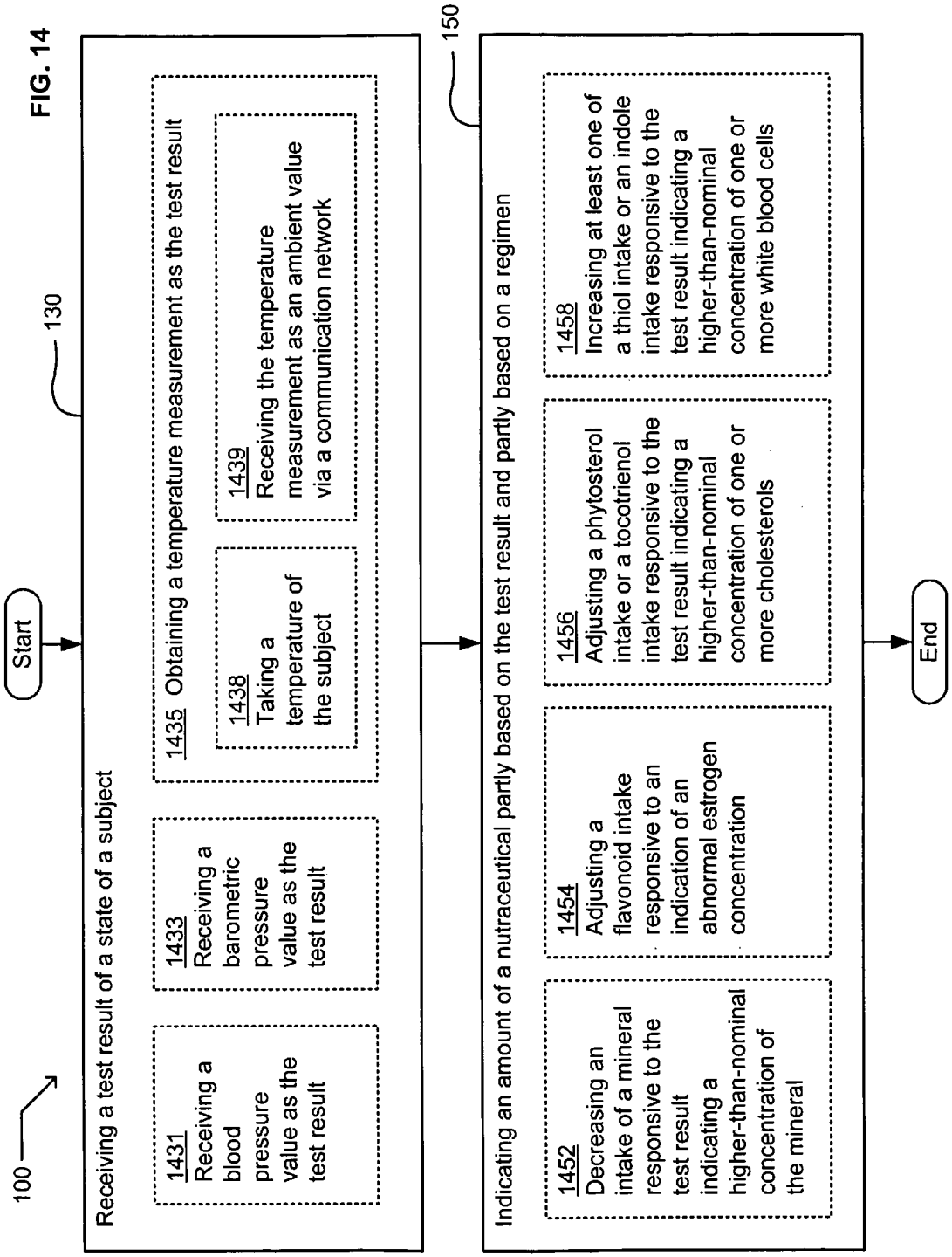

Referring now to FIG. 14, there are shown various optional features of operational flow 100 of FIG. 1. Except as noted, circuitry 430 can optionally perform one or more of operation 1431, operation 1433, operation 1435, operation 1438, or operation 1439 in respective variations of receiving operation 130. Also module 410 can optionally perform one or more of operation 1452, operation 1454, operation 1456, or operation 1458 in respective variations of indicating operation 150. Any of these additional operations can provide unexpected enhancements in health management when performed in configurations like those described above with reference to FIGS. 2-5.

In these configurations, the test result received at operation 130 can include an environmental attribute or a result more specific to the subject. Optional operation 1431, for example comprises receiving a blood pressure value as the test result. Alternatively or additionally, operation 130 can include operation 1433 comprises receiving a barometric pressure value as the test result.

Optional operation 1435 comprises obtaining a temperature measurement as the test result. This can be performed such as by taking a temperature of the subject (at operation 1438 via sensor 485, e.g.) or by receiving the temperature measurement as an ambient value via a communication network (at operation 1439, e.g.).

Optional operation 1452 comprises decreasing an intake of a mineral responsive to the test result indicating a higher-than-nominal concentration of the mineral. The mineral can be sodium, calcium, potassium, or lithium, for example, or some compound or mixture containing the mineral. The intake can be decreased, for example, by reducing a prescribed amount or by suggesting that the subject create or reduce a daily limit of the mineral, compound or mixture. The form of the intake may be a compound that is in a form that differs chemically from a mineral form of the indication. The intake may relate to a salt of the mineral, being decreased responsive to the test result indicating a higher-than-nominal concentration of the mineral in elemental form. The decrease can be a partial decrease or a decrease to zero, and can be permanent or temporary.

Optional operation 1454 comprises adjusting a flavonoid intake responsive to an indication of an abnormal estrogen concentration. Optional operation 1456 comprises adjusting a phytosterol intake or a tocotrienol intake responsive to the test result indicating a higher-than-nominal concentration of one or more cholesterols. Optional operation 1458 comprises increasing at least one of a thiol intake or an indole intake responsive to the test result indicating a higher-than-nominal concentration of one or more white blood cells. Lay-persons and persons of skill in the art can readily design and implement numerous variations and conditional regimens in light of the teachings herein.

Figure 15:
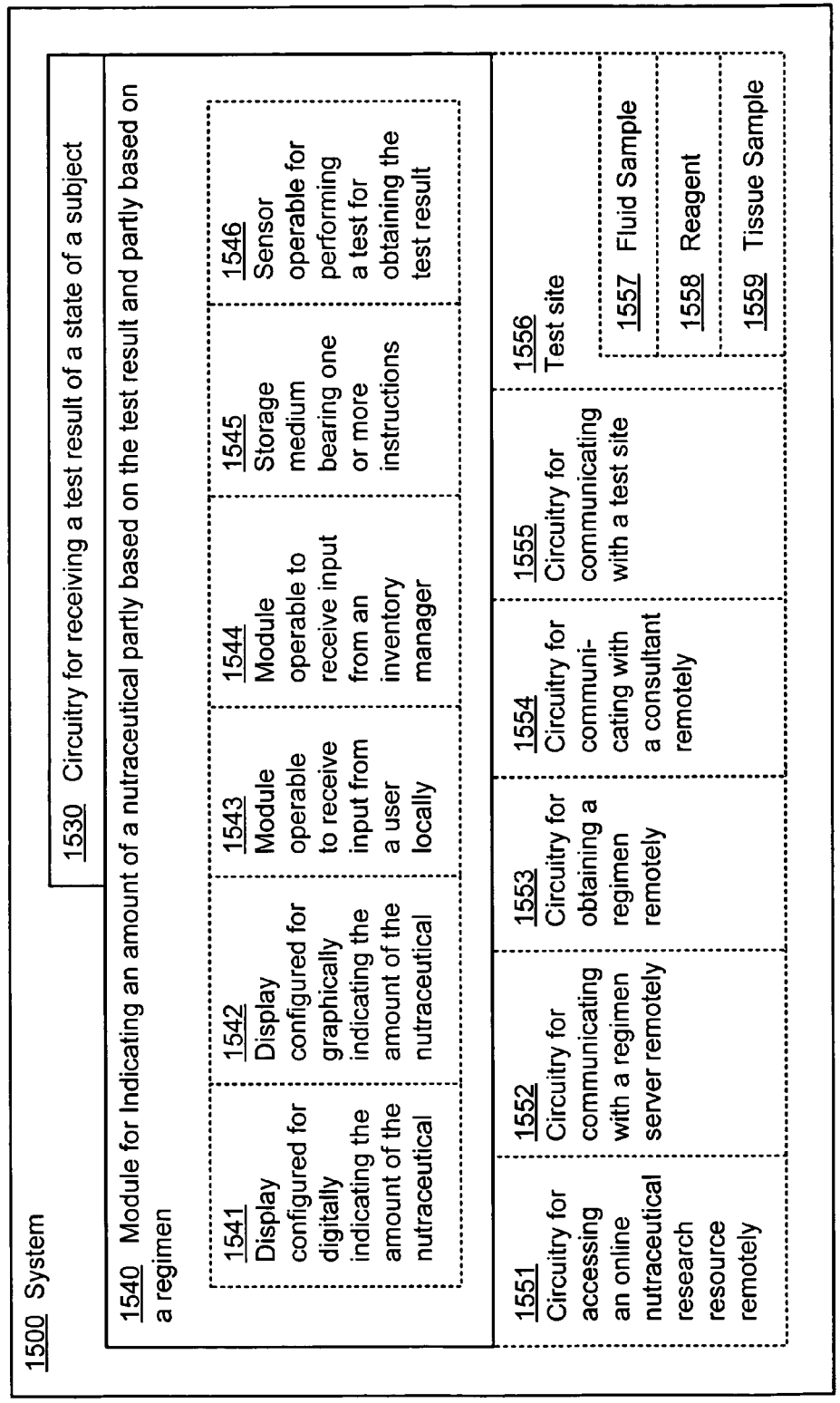
FIG. 15 shows a system operable for performing the flow of FIG. 1, including several optional elements able to perform variants of that flow.

Referring now to FIG. 15, there is shown a system 1500 comprising circuitry 1530 for receiving a test result of a state of a subject, module 1540 for indicating an amount of a nutraceutical partly based on the test result and partly based on a regimen, and various optional features. As shown, for example, module 1540 can include display 1541 configured for digitally indicating the amount of the nutraceutical. Alternatively or additionally, module 1540 can include a display 1542 configured for graphically indicating the amount of the nutraceutical, such as by showing an image including one or more capsules.

Other variations of module 1540 can include one or more of module 1543 operable to receive input from a user locally, module 1544 operable to receive input from an inventory manager, storage medium 1545 bearing one or more instructions, or sensor 1546 operable for performing a test for obtaining the test result.

In addition to circuitry 1530 and module 1540, system 1500 can include one or more of circuitry 1551 for accessing an online nutraceutical research resource remotely, circuitry 1552 for communicating with a regimen server remotely, circuitry 1553 for obtaining a regimen remotely, circuitry 1554 for communicating with a consultant remotely, or circuitry 1555 for communicating with a test site. Alternatively or additionally, system 1500 can include a test site 1556. As shown, test site 1556 can be operable to receive a fluid sample 1557, operable to receive a tissue sample 1559, or operable to receive a sample 1557, 1559 in contact with a reagent 1558.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Moreover, "can" and "optionally" and other permissive terms are used herein for describing optional features of various embodiments. These terms likewise describe selectable or configurable features generally, unless the context dictates otherwise.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interactable and/or logically interacting components.

While certain features of the described implementations have been illustrated as disclosed herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. A system comprising:
   means for receiving at least one test result of at least one parameter of at least one subject following implementation by the at least one subject of at least one subscription-based nutraceutical regimen associated with at least one nutraceutical consumption schedule and at least one performance indicator; and
   means for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen.

2. The system of claim 1, wherein the means for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:

processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and determining at least one nutraceutical adjustment.

3. The system of claim 1, wherein the means for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:

means for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and suggesting at least one order.

4. The system of claim 1, wherein the means for receiving at least one test result of at least one parameter of at least one subject following implementation by the at least one subject of at least one subscription-based nutraceutical regimen associated with at least one nutraceutical consumption schedule and at least one performance indicator comprises:

means for receiving at least one test result of at least one parameter of at least one subject following implementation by the at least one subject of at least one subscription-based nutraceutical regimen identified based at least partly on one or more attributes of the at least one subject and associated with at least one nutraceutical consumption schedule and at least one performance indicator.

5. The system of claim 1, wherein the means for receiving at least one test result of at least one parameter of at least one subject following implementation by the at least one subject of at least one subscription-based nutraceutical regimen associated with at least one nutraceutical consumption schedule and at least one performance indicator comprises:

means for receiving at least one test result of at least one parameter of at least one subject and at least some biometric data of the at least one subject following implementation by the at least one subject of at least one subscription-based nutraceutical regimen associated with at least one nutraceutical consumption schedule and at least one performance indicator.

6. A system comprising:

circuitry configured for receiving at least one test result of at least one parameter of at least one subject following implementation by the at least one subject of at least one subscription-based nutraceutical regimen associated with at least one nutraceutical consumption schedule and at least one performance indicator; and circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with subscription-based nutraceutical regimen.

7. The system of claim 6, wherein the circuitry configured for receiving at least one test result of at least one parameter of at least one subject following implementation by the at least one subject of at least one subscription-based nutraceutical regimen associated with at least one nutraceutical consumption schedule and at least one performance indicator comprises:

circuitry configured for receiving at least one temperature measurement of at least one subject following implementation by the at least one subject of at least one subscription-based nutraceutical regimen associated with at least one nutraceutical consumption schedule and at least one performance indicator.

8. The system of claim 6, wherein the circuitry configured for receiving at least one test result of at least one parameter of at least one subject following implementation by the at least one subject of at least one subscription-based nutraceutical regimen associated with at least one nutraceutical consumption schedule and at least one performance indicator comprises:

circuitry configured for receiving in response to one or more prompts at least one test result of at least one parameter of at least one subject following implementation by the at least one subject of at least one subscription-based nutraceutical regimen associated with at least one nutraceutical consumption schedule and at least one performance indicator.

9. The system of claim 6, further comprising:
   circuitry configured for storing the at least one test result of the at least one parameter of the at least one subject with other medical history data associated with the at least one subject.

10. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:
   circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and determining at least one nutraceutical adjustment and at least partly based on medical history data associated with the at least one subject.

11. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:
   circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and determining at least one nutraceutical at least partly based on data associated with one or more other individuals.

12. The system of claim 6, further comprising:
   circuitry configured for receiving at least one indication of at least one nominal quantity of at least one nutraceutical within at least one delivery unit.

13. The system of claim 6, further comprising:
   circuitry configured for receiving input from at least one inventory manager.

14. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:
   circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and providing access to at least one online resource.

15. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:
   circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and communicating with at least one consultant.

16. The system of claim 6, wherein the circuitry configured for receiving at least one test result of at least one parameter of at least one subject following implementation by the at least one subject of at least one subscription-based nutraceutical regimen associated with at least one nutraceutical consumption schedule and at least one performance indicator comprises:
   circuitry configured for receiving at least one test result of one or more fluid samples of at least one subject following implementation by the at least one subject of at least one subscription-based nutraceutical regimen associated with at least one nutraceutical consumption schedule and at least one performance indicator.

17. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:

circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and determining at least one nutraceutical adjustment at least partly based on input associated with the at least one subject.

18. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:

circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and ordering at least one nutraceutical.

19. The system of claim 6, further comprising:
circuitry configured for monitoring nutraceutical inventory.

20. The system of claim 6, wherein the circuitry configured for receiving at least one test result of at least one parameter of at least one subject following implementation by the at least one subject of at least one subscription-based nutraceutical regimen associated with at least one nutraceutical consumption schedule and at least one performance indicator comprises:

circuitry configured for receiving at least one visible attribute of at least one subject following implementation by the at least one subject of at least one subscription-based nutraceutical regimen associated with at least one nutraceutical consumption schedule and at least one performance indicator.

21. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:

circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and determining at least one nutraceutical adjustment at least partly based on input from at least one health-care worker.

22. The system of claim 6, further comprising:
circuitry configured for transmitting information associated with the at least one test result of the at least one parameter of the at least one subject for recordance in at least one medical record associated with the at least one subject.

23. The system of claim 6, wherein the circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen comprises:

circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen and identifying at least one health-care provider.

24. The system of claim 6, further comprising:
circuitry configured for signaling dispensation of at least one amount of at least one nutraceutical.

25. The system of claim 6, wherein the circuitry configured for receiving at least one test result of at least one parameter of at least one subject following implementation by the at least one subject of at least one subscription-based nutraceutical regimen associated with at least one nutraceutical consumption schedule and at least one performance indicator comprises:

circuitry configured for receiving at least one test result of at least one parameter of at least one subject and at least some biometric data of the at least one subject following implementation by the at least one subject of at least one subscription-based nutraceutical regimen associated with at least one nutraceutical consumption schedule and at least one performance indicator.

26. The system of claim 6, further comprising:
circuitry configured for publishing the at least one performance indicator in association with the at least one subscription-based nutraceutical regimen, the at least one performance indicator being based at least partly on data from one or more subscribers.

27. The system of claim 6, further comprising:
circuitry configured for disseminating the at least one subscription-based nutraceutical regimen associated with the at least one nutraceutical consumption schedule and the at least one performance indicator to the at least one subject in response to at least one subscription enrollment.

28. The system of claim 27, further comprising:
circuitry configured for publishing the at least one updated performance indicator in association with the at least one subscription-based nutraceutical regimen.

29. A device comprising:
circuitry configured for receiving at least one test result of at least one parameter of at least one subject following implementation by the at least one subject of at least one subscription-based nutraceutical regimen associated with at least one nutraceutical consumption schedule and at least one performance indicator; and
circuitry configured for processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen.

30. One or more non-transitory computer-readable media bearing one or more executable instructions for facilitating operations comprising:
receiving at least one test result of at least one parameter of at least one subject following implementation by the at least one subject of at least one subscription-based nutraceutical regimen associated with at least one nutraceutical consumption schedule and at least one performance indicator; and
processing the at least one test result of the at least one parameter of the at least one subject including comparing the at least one test result of the at least one parameter of the at least one subject to at least one previous test result of the at least one parameter of the at least one subject and based at least partly on at least one result of comparing the at least one test result of the at least one parameter of the at least one subject to the at least one previous test result of the at least one parameter of the at least one subject, updating the at least one performance indicator associated with the at least one subscription-based nutraceutical regimen.

* * * * *

UNITED STATES PATENT AND TRADEMARK OFFICE
CERTIFICATE OF CORRECTION

PATENT NO.         : 8,532,938 B2                                             Page 1 of 1
APPLICATION NO.    : 11/291532
DATED              : September 10, 2013
INVENTOR(S)        : Edward K. Y. Jung et al.

It is certified that error appears in the above-identified patent and that said Letters Patent is hereby corrected as shown below:

In the Claims

In Column 20, Line 38-39, Claim 6 please delete text "performance indicator associated with subscription-based" and replace with --performance indicator associated with the at least one subscription-based--

In Column 25, Line 9, Claim 27 please delete "The system of claim 6" and replace with --The system of claim 26--

Signed and Sealed this
Twenty-second Day of April, 2014

Michelle K. Lee
*Deputy Director of the United States Patent and Trademark Office*